(12) United States Patent
Tachikawa et al.

(10) Patent No.: US 7,368,277 B2
(45) Date of Patent: May 6, 2008

(54) METHOD FOR ASSAY OF ANTIBODIES AND ANTIBODY ASSAY DEVICE

(75) Inventors: Tetsuya Tachikawa, Tokushima (JP); Atsunari Noda, Tokushima (JP); Kiyonori Katsuragi, Tokushima (JP)

(73) Assignee: Otsuka Pharmaceutical Factory, Inc., Tokyo (JP)

( * ) Notice: Subject to any disclaimer, the term of this patent is extended or adjusted under 35 U.S.C. 154(b) by 0 days.

(21) Appl. No.: 10/386,562

(22) Filed: Mar. 13, 2003

(65) Prior Publication Data
US 2003/0175699 A1    Sep. 18, 2003

Related U.S. Application Data

(63) Continuation of application No. 09/445,565, filed as application No. PCT/JP99/01921 on Apr. 9, 1999, now abandoned.

(30) Foreign Application Priority Data

Apr. 14, 1998    (JP) ............................... 10-103095
Apr. 28, 1998    (JP) ............................... 10-118524
Aug. 3, 1998    (JP) ............................... 10-218843

(51) Int. Cl.
*A63B 69/18* (2006.01)

(52) U.S. Cl. .................. 435/252.8; 435/7.1; 435/7.21; 435/7.37; 435/7.9; 435/7.92; 435/7.93; 435/7.94; 435/7.95; 435/252.33; 435/849; 435/948; 435/962; 435/960; 436/518; 436/824

(58) Field of Classification Search ............ 435/7.1, 435/7.21, 7.37, 7.9, 7.92–7.95, 252.33, 252.8, 435/849, 948, 960, 962; 436/518, 824
See application file for complete search history.

(56) References Cited

U.S. PATENT DOCUMENTS

| | | | |
|---|---|---|---|
| 4,435,504 A | 3/1984 | Zuk et al. | |
| 4,469,787 A | 9/1984 | Woods et al. | |
| 4,623,461 A | 11/1986 | Hossom et al. | |
| 4,632,901 A | 12/1986 | Valkirs et al. | |
| 4,703,017 A | 10/1987 | Campbell et al. | |
| 4,861,711 A | 8/1989 | Friesen et al. | |
| 4,929,543 A | 5/1990 | Kientsch-Engel et al. | |
| 4,938,927 A | 7/1990 | Kelton et al. | |
| 5,073,484 A | 12/1991 | Swanson et al. | |
| 5,120,662 A | 6/1992 | Chan et al. | |
| 5,141,875 A | 8/1992 | Kelton et al. | |
| 5,447,837 A | 9/1995 | Urnovitz | |
| 5,496,520 A | 3/1996 | Kelton et al. | |
| 5,591,645 A | 1/1997 | Rosenstein | |
| 5,602,040 A | 2/1997 | May et al. | |
| 5,622,871 A | 4/1997 | May et al. | |
| 5,654,162 A | 8/1997 | Guire et al. | |
| 5,656,503 A | 8/1997 | May et al. | |
| 5,714,389 A | 2/1998 | Charlton et al. | |
| 5,846,751 A | 12/1998 | Pronovost et al. | |
| 5,985,599 A | 11/1999 | McKenzie et al. | |

FOREIGN PATENT DOCUMENTS

| | | |
|---|---|---|
| DE | 195 16 466 | 11/1995 |
| JP | 63305249 | 12/1988 |
| JP | 5-180837 | 7/1993 |
| JP | 9-500962 | 1/1997 |
| JP | 5-340947 | 12/1998 |
| WO | WO 92 08809 | 5/1992 |
| WO | WO 92 22797 | 12/1992 |
| WO | WO 95/02822 | 1/1995 |
| WO | WO 95 30902 | 11/1995 |

OTHER PUBLICATIONS

Chart et al, *J. of Microbiology Methods.*, 28:85-88 (1997).
Katsuragi et al, *Helicobacter.*, 3(4):289-295 (1998).
Brade et al, *Infect. and Immun.*, 65(9):3961-3965 (1997).
*Clinical and Diagnostic Laboratory Immunology*, 5(1):24-27 (1998)—Takahasi.
Dhar et al, *Diagn. Microbiol. Infect. Dis.*, 30(1):1-6 (1998).
Figura et al, *Microbiologica*, 17(4):319-325 (1994).
Loeb et al, *Can. J. Gastroenterol.*, 11(5):437-440 (1997).
Ching et al, *Postgrad. Med. J.*, 69(812):456-460 (1993).
Jensen et al, *APMIS*, 101(10):795-801 (1993).
Amini et al, *FEMS Immunol. Med. Microbiol.*, 16(3-4):163-172 (1996).
Reimer et al, *Hybridoma*, 3(3):263-275 (1984).
Girkontaite et al, *Cancer Biother. Radiopharm.*, 11(1)87-96 (1996).
Yoshihara et al., Clinical usefulness of urinary anti HIV antibody test—a large scale study from 11 institutes in Japan. *Rinsho Byori* 43(3):249-256 (1995)—Abstract only.
Van Nerom et al., Monoclonal and polyclonal antibodies to chicken immunoglobulin isotypes specifically detect turkey immunoglobulin isotypes. *Vet Immunol Immunopathol.* 57(3-4):305-314 (1997).
Gandhi et al., Enzyme linked protein-A: an ELISA for detection of amoebic antibody. *Trans R Soc Trop Med Hyg.* 81(2):183-185 (1987).
Alemohammad et al., Detection of immunoglobulin G antibodies to *Helicobacter pylori* in urine by an enzyme immunoassay method. *J. Clin. Microbiol.* 31(8):2174-2177 (1993).

*Primary Examiner*—Bao-Thuy L. Nguyen
(74) *Attorney, Agent, or Firm*—Sughrue Mion, PLLC

(57) ABSTRACT

The invention relates to a technology by which antibodies directed to sources of infection in body fluids can be assayed with high accuracy, expediency and specificity. More particularly, the invention provides an antibody immunoassay method in which the antigen-antibody reaction between a target antibody in a sample and an assay antigen is conducted in the presence of an *E. coli* component and an antibody assay method which comprises using a reagent having a specific affinity for the Fc region of an antibody IgG as the antibody assay reagent. The invention further provides an antibody assay device comprising a solid-phase support having at least (a) a first region to which a sample is applied and (b) a second region where the antibody in the sample is reacted as disposed in such an arrangement that the sample is wicked from the first region to the second region and a labeling means for detection of the result of the reaction in the second region, characterized in that the (b) second region is provided with (i) a test site in which a ligand for capturing the target antibody to be assayed is immobilized and (ii) a control site in which a ligand for capturing an arbitrary antibody occurring in the sample is immobilized.

10 Claims, 12 Drawing Sheets

F I G . 1
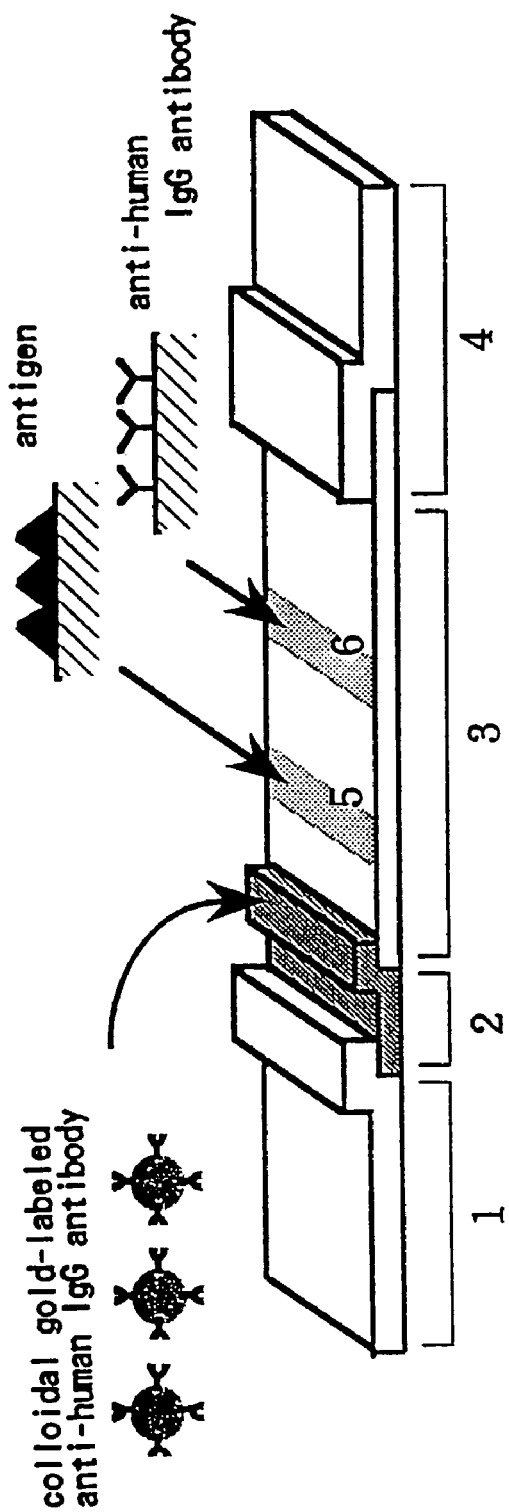

(A)

(B)

F I G . 4
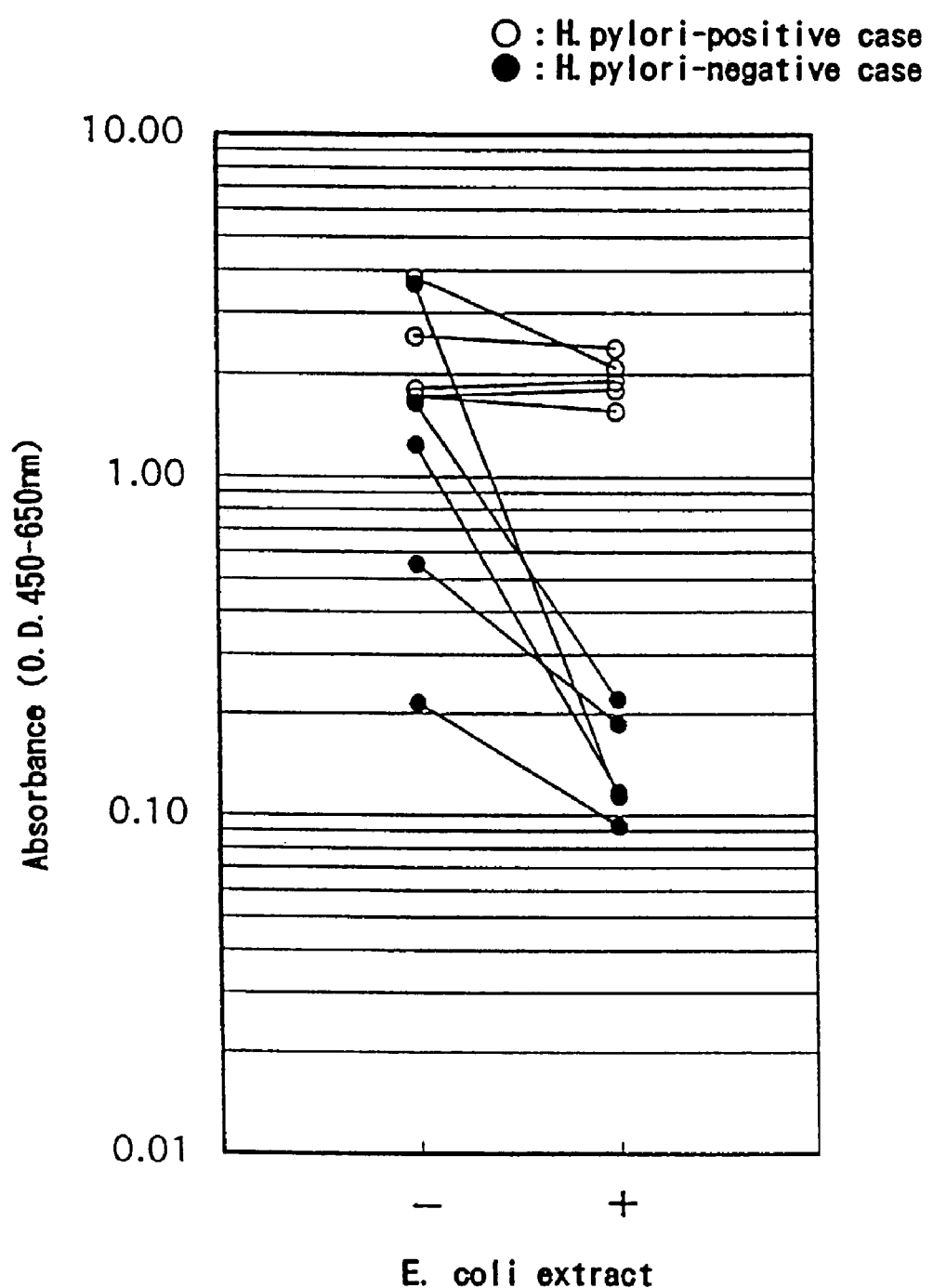

METHOD FOR ASSAY OF ANTIBODIES AND ANTIBODY ASSAY DEVICE

This application is a Continuation of U.S. application Ser. No. 09/445,565, filed Dec. 9, 1999, (now abandoned) which is a 371 of PCT/JP99/01921, filed Apr. 9, 1999, the disclosure of each of which is incorporated herein by reference.

TECHNICAL FIELD

The present invention relates to a method of detecting or quantitating antibodies in samples and more particularly to a method by which antibodies against sources of infection such as bacteria and viruses as occurring in clinical body fluid samples, particularly urine samples, can be detected or assayed with high accuracy, expediently, and with good specificity.

The present invention in a further aspect relates to a device for detecting or quantitating an antibody in a sample and more particularly to a device with which the antibody against a source of infection as occurring in clinical body fluid samples, particularly urine samples, can be detected or assayed with high accuracy, expediently, and with good specificity.

The invention further relates to an antibody assay reagent kit which is useful for the above antibody assay method and the assay method using said antibody assay device.

BACKGROUND ART

Detection of antibodies specific to various sources of infection (pathogens) such as bacteria and viruses, which may occur in body fluids, is a useful indirect means for the diagnosis of an infection. Therefore, immunological assay techniques and devices designed to detect an antibody by utilizing a pathogen or a component of the pathogen as an assay antigen have heretofore been used in a broad field of diagnosis.

Such an immunoassay method using a pathogen or a component thereof as an assay antigen is advantageous in that the necessary assay system can be easily established but is not fully satisfactory in sensitivity and specificity, thus leaving room for improvement.

As an immunoassay device for use in such immunological assays, there can be mentioned a strip of porous material on which a binding assay (antigen-antibody reaction) is carried out. An assay device of this type takes advantage of the capillary property of a porous substrate, that is to say a body fluid applied to one end of a porous strip migrates toward the other end. Thus, when a test sample (liquid) containing a substance to be assayed is applied to one end of the strip carrying various reagents disposed successively in strategical positions, the sample migrates by capillary action along the strip and encounters those reagents in said positions in succession to undergo reactions. The existence of the substance to be assayed can be confirmed and its amount be determined by detecting a signal from the detectable label included in the ligand-receptor coupling system.

The immunoassay technique utilizing the above principle is often called immunocapillary assay or imunochromatographic assay, and has been described in WO No.87/02774, EP No.0306772 and other publications. As to modifications of the technique, the inventions described in Japanese Unexamined Patent Publication NO.63865/1989, Japanese Unexamined Patent Publication NO.299464/1989 and Japanese Unexamined Patent Publication NO.167497/1994 can be mentioned.

The above-mentioned device is advantageous in that no specific instrument is required for determination and the assay can be completed easily and within a short time but have room for improvement in sensitivity and specificity.

In addition, because the device performs one test only, a negative or positive control sample cannot be concurrently determined, with the consequent disadvantage that it is impossible to judge whether the result is a reliable data generated by the proper determination.

Generally speaking, urine and saliva, among body fluids, are favored as clinical test samples because its collection requires no invasive procedure and is easy and safe as compared with blood.

However, it is usual that the concentrations of antibodies present in such samples are extremely low, for example of the order of one-thousandth to one-ten thousandth of the concentrations in blood. In addition, urine samples collected from subjects who have taken large quantities of water are extremely thin, with the result that a large variation is inevitable in antibody titer among samples.

In such cases, with the conventional assay device described above, the test will be negative when the sample is too thin to detect an antibody, so that the problem arises that the case of "true negative" cannot be differentiated from the case of "negative (false negative)" occasioned by the low concentration of the sample.

Furthermore, when samples lean in antibodies are to be tested, a highly sensitive assay system is required but in that case there is the problem that byproducts formed by non-specific reactions due to contaminants in the samples are liable to be simultaneously detected to give false positive results.

Therefore, an antibody assay system insuring sufficiently high detection sensitivity even when such body fluids as urine and saliva are used as samples, that is to say a reliable assay system contributory to reduced chances for false negative and false positive tests because of high specificity, is required.

The first object of the present invention is to provide an antibody assay technology (antibody assay method and antibody assay device) which is capable of detecting antibodies against sources of infection occurring in test samples such as body fluids with high sensitivity and high specificity.

The second object of the present invention is to provide an antibody assay method which enables determinations with high accuracy through suppression of "false positive" reactions arising from contaminants in samples even when the samples are those of urine or other body fluid which are comparatively lean in the target antibody.

The third object of the present invention is to provide an antibody assay method as an improvement in immunocapillary assay or immunochromatographic assay, by which the existence and amount of the target antibody as the object of detection in a sample can be accurately determined with a clear demarcation between a "false negative reaction" arising from the nature of the sample and a "true negative" reaction.

BRIEF DESCRIPTION OF THE DRAWINGS

FIG. 1 is a diagram showing a solid phase support in the form of a strip as a constituent element of the antibody assay device of the invention. In FIG. 1, the code 1 represents a first region, 2 a tracer region, 3 a second region, 4 a third region, 5 a test zone and 6 a control zone.

In FIG. 3, the codes 1~6 have the same meanings as in FIG. 1, and the code 7 represents an upper section of the housing, 8 a lower section of the same, 9 a sample inlet port, and 10 a detection window.

FIG. 4 is a diagrammatic representation of the results of determination of anti-*H. pylori* antibody in urine in Example 1 (5) (i). In FIG. 4, the open circles represent data on urine samples from subjects with *H. pylori* infection who gave a positive $^{13}$C-UBT test and the closed circles represent data on urine samples from subjects who gave a negative $^{13}$C-UBT test.

In FIG. 5, the ordinate represents absorbance (O.D. 450 nm) and the abscissa represents the *H. pylori*-positive and *H. pylori*-negative groups established according to the $^{13}$C-UBT test.

In FIG. 6, open circles represent data on urine samples from subjects who gave a positive $^{13}$C-UBT test and closed circles represent data on urine samples from subjects who gave a negative $^{13}$C-UBT test.

In FIG. 7, closed circles represent data on urine samples from subjects who gave a positive test for blood anti-HBc antibody and open circles represent data on urine samples from subjects who gave a negative test for blood anti-HBc antibody.

In FIG. 8, the ordinate represents absorbance (O.D.) and the abscissa represents the gel permeation chromatographic fraction (fraction No.). The solid line represents the absorbance of the protein at 280 nm, the black dot-line represents data generated with anti-human (IgG+IgM) antibody, open triangle-line represents data generated with anti-human IgG (Fc-specific) antibody; and the closed triangle-line represents data generated with anti-human IgG (Fab-specific) antibody.

In FIG. 9, the ordinate represents absorbance (O.D. 450~650 nm) and the abscissa represents the *H. pylori*-positive group (+: n=56) and -negative group (−: n=44) as classified by the $^{13}$C-UBT test.

In FIG. 10, the ordinate represents absorbance (O.D. 450~650 nm) and the abscissa represents the anti-rubella antibody-positive group (+: n=76) and -negative group (−: n=23) as classified according to the serum level measured with a commercial kit.

In FIG. 12, "Specificity" represents the percentage of negative tests (negative rate) relative to the total number of tests when samples from subjects verified by the $^{13}$C-UBT test to be negative were determined for each test item with each assay device and "Sensitivity" represents the percentage of positive tests (positive rate) relative to the total number of tests when samples from subjects verified by the $^{13}$C-UBT test to be positive were determined for each test item with each assay device. The control devices A~H mean the following devices.

Figure 2:
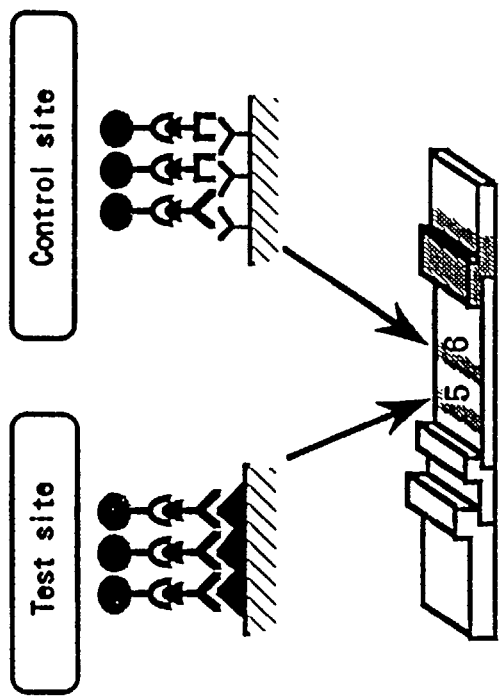
FIG. 2 is a diagram illustrating the principle of assay of the target antibody in a sample with the antibody assay device of the invention. The respective codes used have the same meanings as in FIG. 1.
Figure 2:
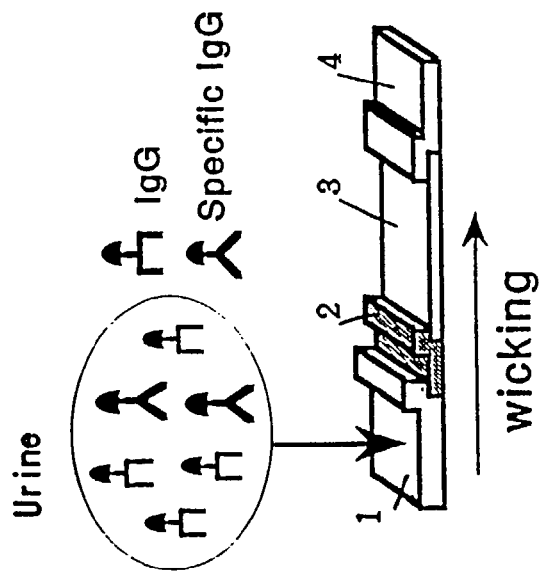

| | |
|---|---|
| A: | Helitest (manufactured by Cortecs Diagnostics) |
| B: | *H. pylori*-Check-1 (manufactured by Bio-Medical Products) |
| C: | First Check *H. pylori* (manufactured by Worldwide Medical Corp) |
| D: | Biocard *Helicobacter pylori* IgG (manufactured by Anti Biotech Oy) |
| E: | Insta Test *H. Pylori* (manufactured by Cortez Diagnostics Inc.) |
| F: | One Step *H. pylori* Test (manufactured by Teco Diagnostics) |
| G: | *H. pylori* SPOT (manufactured by International Immuno-Diagnostics) |
| H: | Quick Stripe *H. pylori* (manufactured by Diatech Diagnostics Inc.) |

DISCLOSURE OF INVENTION

The inventors of the present invention did much research for establishing an assay system which would enable high-precision determination of target antibodies even when samples are lean in the antibodies, for example urine samples, and found that an antibody component which nonspecifically binds the antigen in an antigen-antibody reaction (hereinafter referred to as the nonspecific binding antibody component) exists in the assay system to give rise to nonspecific reactions, thus causing a false positive result and hence lowering the accuracy of detection.

Based on the above findings the inventors did further research and found that said nonspecific reactions can be suppressed by conducting the antigen-antibody reaction between the target antibody to be assayed and the antigen specific to the particular antibody in the presence of an *Escherichia coli* (*E. coli*) component, whereby the false positive rate can be reduced to achieve a significant improvement in the accuracy of detection.

The inventors further discovered that said nonspecific binding antibody component comprises IgG fragments and/or their denaturation products which retain the antigenicity of the light (L) chain or F (ab) region of the IgG and that this antibody component cross-reacts with the ordinary antibody assay reagents (e.g. secondary antibodies) used in serum antibody assay systems, thus leading to false positive tests.

Based on the above findings, the inventors of the present invention further confirmed that the nonspecific reactions in an antibody assay system can be inhibited by using a reagent having a specific affinity for the Fc region of the assay target antibody IgG as an antibody assay reagent, whereby the false positive rate can be reduced to improve the accuracy of detection in a significant degree.

Meanwhile, the inventors endeavored to improve the antibody assay hardware (the immunocapillary assay device and immunochromatographic assay device) and found that "true negative" reactions can be accurately detected excluding "false negative" reactions by establishing a "control site" for detecting an arbitrary antibody in samples in addition to the site (test site) for detecting the target antibody in the reaction zone (evaluation zone) of the strip as a part of the assay device. Thus, in such an assay system, when the sample is an inappropriate sample which cannot be assayed for reasons such as too low a concentration of the antibody (that is to say the total amount of the antibody is too small), the "control site" gives a negative signal indicating that the sample is not assayable. On the other hand, when the sample has an appropriate antibody concentration, the "control site" gives a positive signal indicating that the sample is appropriate for the intended assay of the target antibody. Then, according to the result in this "test site", one may know for certain the presence or absence of the target antibody in the sample, that is to say whether the sample is "positive" or "true negative".

In this connection, Japanese Unexamined Patent Publication NO.299464/1989 and Japanese Unexamined Patent Publication NO.167497/1994, both disclosing improvements in the antibody assay hardware (immunocapillary assay device and immunochromatographic assay device), describe the devices including a control site in addition to a test site. However, the control site in these devices is designed to ascertain whether or not a label disposed in an upstream region of the strip has traversed through the test site by capillary action and, therefore, is quite different from the control site in accordance with the invention.

The present inventors further confirmed that when the coupling reaction between the target antibody and the corresponding antigen by means of the above improved antibody assay device is conducted in the presence of an *E. coli* component, the nonspecific reaction in this antigen-antibody reaction system is inhibited and that when a reagent having a specific affinity for the Fc region of the IgG is used as the antibody assay reagent, the nonspecific reaction with the antigen-antibody complex is inhibited, thus leading to a significant decrease in the incidence of a false-positive test.

The present invention has been developed on the basis of the above several findings.

In a first aspect thereof, the present invention provides a high-precision method for assaying an antibody with a reduced incidence of false positive reaction.

(1-1) As one mode thereof, the above antibody assay method for detecting a target antibody in a sample by utilizing an antigen-antibody reaction is characterized in that said reaction is carried out between said antibody and an assay antigen in the presence of an *E. coli* component.

This method for assaying an antibody includes the following specific methods.

(a) The antibody assay method in which said *E. coli* component is at least one member selected from the group consisting of the soluble fraction and lipopolysaccharide fraction of *Escherichia coli*.

(b) The antibody assay method wherein the *E. coli* component is used in a proportion of about 0.1~100 μg, preferably about 0.5~50 μg, per μg of the assay antigen.

(1-2) As another mode, the antibody assay method comprises detecting a target antibody in a sample by the sandwich technique, characterized in that a reagent comprising a secondary antibody having a specific affinity for the Fc region of the target antibody IgG is used as an antibody assay reagent.

This method for assaying an antibody includes the following specific methods.

(a) The antibody assay method in which the secondary antibody is an Fc-specific anti-IgG antibody.

(b) The antibody assay method comprising an antigen-antibody reaction step in which the target antibody in the sample is coupled to an immobilized antigen specific to said antibody as immobilized on a support and a reaction step in which the target antibody captured by said immobilized antigen is reacted with a secondary antibody having a specific affinity for the Fc region of the antibody IgG.

(c) The above antibody assay method in which the antigen-antibody reaction is carried out in the presence of an *E. coli* component.

In a second aspect, the present invention relates to an antibody assay device. This device includes the following embodiments.

(2-1) An antibody assay device comprising a solid phase support having at least (a) a first region to which a sample is applied and (b) a second region in which the antibody in the test sample is reacted as arranged in such a sequence that the sample is transported from the first region to the second region by capillary action, and a labeling means for detecting the result of reaction in the second region, said (b) second region having (i) a test site where a ligand for capturing the target antibody to be detected has been immobilized and (ii) a control site where a ligand for capturing an arbitrary antibody in the sample has been immobilized.

(2-2) The antibody assay device wherein the ligand immobilized in the test site is an antigen to the target antibody occurring in the sample.

(2-3) The antibody assay device wherein the ligand immobilized in the control site is an anti-human immunoglobulin antibody capable of capturing an arbitrary antibody in the sample.

(2-4) The antibody assay device comprising a labeled ligand to be bound by both the target antibody and arbitrary antibody as said labeling means.

(2-5) The antibody assay device wherein the labeling means is a labeled ligand to be bound by both the target antibody and arbitrary antibody as removably supported upstreams of the second region of the solid phase support in such a manner that, upon contact with a sample, it reacts with the target antibody and arbitrary antibody to form a target antibody/labeled ligand complex and an arbitrary antibody/labeled ligand complex, respectively, which are then transported by capillary action to the second region where they are fixed in the test site and control site, respectively.

(2-6) The antibody assay device wherein the labeled ligand is supported in a region (tracer region) intermediate between the first region and second region of the solid phase support.

(2-7) The antibody assay device wherein the labeled ligand to be bound by both the target antibody and arbitrary antibody is a labeled anti-human immunoglobulin antibody.

(2-8) The antibody assay device wherein the anti-human immunoglobulin antibody is an anti-IgG antibody having a specific affinity for the Fc region of immunoglobulin G.

(2-9) The antibody assay device wherein the solid phase support is further provided with an absorption region downstreams of the first and second regions so that the sample transported from the first region to the second region is further transported by capillary action to the absorption region.

(2-10) The antibody assay device wherein the coupling reaction of the target antibody at the test site in the second region takes place in the presence of an *E. coli* component.

In a third aspect, the present invention relates to a method for solid phase assay of a target antibody in a sample. This method includes the following embodiments.

(3-1) A method for solid phase assay of a target antibody which comprises applying the sample to the first region of the antibody assay device, and detecting the development of a color at the test site in the second region under the condition of the control site in the second region developing a color.

(3-3) The method for solid phase assay of a target antibody wherein the coupling reaction of the target antibody at the test site in the second region of the antibody assay device takes place in the presence of an *E. coli* component.

In a fourth aspect, the present invention relates to an antibody assay reagent kit for use in association with said antibody assay device. The antibody assay reagent kit may include the following embodiments.

(4-1) An antibody assay reagent kit characterized by its comprising an *E. coli* component.

(4-2) The antibody assay reagent kit further comprising an antigen or antibody assay reagent which is optionally immobilized.

(4-3) The antibody assay reagent kit characterized by its containing an Fc-specific anti-IgG antibody as the antibody assay reagent.

(4-4) The antibody assay reagent kit containing the antibody assay device according to the invention.

(1) Antibody Assay Method

In the first place, the antibody assay method as the first aspect of the present invention is now described in detail.

The antibody assay method of the invention represents an improvement in the antibody immunoassay method and is characterized in that the incidence of false positive reaction can be decreased through inhibition of non-specific reaction.

(1-1) As an embodiment of the above antibody assay method, there can be mentioned a method in which the antigen-antibody reaction between the target antibody in a sample and an antigen specific to said antibody is carried out in the presence of an *E. coli* component. In accordance with this method, the nonspecific reaction in the antigen-antibody reaction is significantly inhibited, with the result that the incidence of a false positive test can be decreased.

The *E. coli* component is not particularly restricted provided that it is a component of *Escherichia coli*, thus including but not limited to the protein component, carbohydrate component or lipid component thereof or a mixture of such components. As a preferred example, a soluble fraction or lipopolysaccharide (LPS) fraction of *E. coli* can be mentioned.

There is no particular limitation on the method for preparing such an *E. coli* component but a variety of methods can be selectively used. A usual procedure may comprise growing an arbitrary *E. coli* strain in a medium suited for its proliferation, harvesting the grown cells, and either disintegrating the cells physically by means of a sonicator or solubilizing them with a surfactant or the like to provide a soluble fraction (extract). The LPS mentioned above can be prepared by an extractive procedure using an organic solvent, e.g. phenol, chloroform or ether, or a mixture of two or three different organic solvents. It can also be prepared artificially using a genetic engineering technique. Moreover, commercial products can be expediently utilized (e.g. Lipopolysaccharide *E. coli*. which is available from Difco or Sigma)

The preferred sample to which the invention can be applied is a body fluid sample. The body fluid is not restricted provided that it is a body fluid derived from a human or other animal in which the target antigen is supposedly contained. Thus, the term "body fluid" covers a broad variety of biological fluids which are used as samples in routine laboratory tests. More particularly, the body fluid includes blood, inclusive of serum and plasma, urine, cerebrospinal fluid, amniotic fluid, saliva, sweat, and so forth. Particularly the present invention solves the problem of poor detection accuracy associated with noninvasive samples which are favored as samples for antibody detection, such as urine, saliva and sweat, particularly urine, and, therefore, those biological materials can be mentioned as preferred examples of the body fluid.

The "target antibody" the object of determination, is not particularly restricted provided that it is an antibody the detection of which is desired, thus including antibodies against various sources of infection which are foreign bodies to the host.

The sources of infection are not particularly restricted but include many different pathogens which infect man and other animals and give rise to antibodies in the hosts. More particularly, said pathogen includes a variety of viruses such as HIV (human immunodeficiency virus), type A, B, C and other hepatitis viruses, rubella virus, influenza virus, measles virus, cytomegalovirus, herpes simplex virus, varicella-zoster herpes virus, adenovirus, enterovirus, etc.; bacteria such as *Helicobacter pylori* (hereinafter referred to briefly as *H. pylori*), *Clamydia* spp., *Mycobacterium tuberculosis*, spirochetes, gonococci, *Treponema pallidum, Mycoplasma* spp., etc. (excluding *Escherichia coli*); and protozoae such as *Toxoplasma gondii, Entamoeba histolytica, Rickettsia tsutsugamushi*, and so forth. Preferred are viruses such as HIV, hepatitis viruses, rubella virus, influenza virus, measles virus, herpes virus, etc. and bacteria represented by *Helicobacter pylori* etc., with bacteria such as *H. pylori* being particularly preferred.

The antigen for use in the antibody assay method of the invention is not particularly restricted provided that it is an antigen capable of undergoing antigen-antibody reaction with the target antibody to be detected. Thus, for example, any of the antigens used in the conventional serum antibody assay system can be successfully used. Those antigens may not only be the very pathogens such as said viruses and bacteria but also be antigens having the antigenic determinant groups intrinsic to the respective pathogens. Thus, for example, inactivated pathogens available upon heat treatment or irradiation of pathogens, antigens prepared by extracting pathogens with a surfactant or the like, and antigens artificially prepared by chemical synthesis or recombinant DNA technology.

Incidentally, whether a candidate antigen may be successfully used or not in the assay method of he invention can be easily ascertained typically by testing its reactivity with the target antibody in the conventional manner.

In the assay method of the invention, said antigen may be optionally used as immobilized on an arbitrary solid phase beforehand. The solid phase mentioned just above may be any of the various solid phases in routine use in this field of art, thus including but not limited to sticks, beads, plates (inclusive of microtiter plates) and test tubes made of various materials, for example glass, cellulose powder, Sephadex, Sepharose, polystyrene, filter paper, carboxymethylcellulose, ion exchange resins, dextran, plastic film, plastic tubing, nylon, glass beads, silk, polyamine-methyl vinyl ether-maleic acid copolymer, amino acid copolymer, ethylene-maleic acid copolymer, etc.

The method for immobilization is not particularly restricted, either, but may be whichever of physical bonding and chemical bonding. For example, chemical bonding methods such as covalent bonding methods, e.g. diazo method, peptide method (acid amide derivative method, carboxyl chloride resin method, carbodiimide resin method, maleic anhydride derivative method, isocyanate derivative method, bromocyan activated polysaccharide method, cellulose carbonate derivative method, condensing reagent method, etc.), alkylation method, crosslinking agent coupling method (the method for coupling to a support using glutaraldehyde, hexamethylene isocyanate or the like as the crosslinking agent), Ugi reaction coupling method, etc.; ionic binding methods using ion exchange resins and the like supports; and physical adsorption methods using glass beads or other porous glass supports.

The amount of the antigen to be used in the assay system is not particularly restricted but may be freely selected according to the amount of the antigen which is in routine use for the particular assay system. For example, when the sandwich method is used, generally the antigen is used in excess over the target antibody. Taking the case in which the reaction is conducted in a 100 µl reaction system as an example, the antigen may be used in a proportion of generally about 0.1~100 µg/ml, preferably about 1~10 µg/ml.

The conditions of the antigen-antibody reaction between said antigen and target antibody are not particularly restricted but may be the same as those in routine use for conventional immunoassays except that the reaction should be conducted in the presence of an $E.\ coli$ component. A typical procedure may comprise incubating or allowing to stand said antigen, antibody and $E.\ coli$ component together at a temperature of generally not higher than 45° C., preferably about 4~40° C., more preferably about 25~40° C., for about 0.5~40 hours, preferably about 1~20 hours. The solvent for use in the reaction and its pH are not particularly restricted, either, as far as the reaction is not interfered with. Thus, the conventional buffers showing a buffer action in the pH range of about 5~9, such as citrate buffer, phosphate buffer, tris buffer, acetate buffer, etc. can be used generally in the routine manner.

The proportion of the $E.\ coli$ component in this reaction system is not particularly restricted but may for example be generally about 0.1~100 µg, preferably about 0.5~50 µg, per µg of the antigen in the reaction system.

The procedure for practicing the antibody assay method of the invention is not particularly restricted except for the basic requirement that it comprises an antigen-antibody reaction step in which the target antibody is reacted with the corresponding antigen, which may be an immobilized antigen, in the presence of said $E.\ coli$ component. Preferably, however, the method further comprises a step of detecting the target antibody captured by said antigen (antigen-antibody complex), that is to say a step of reacting the antigen-antibody complex with an antibody assay reagent.

The method of detecting and quantitating the antigen-antibody complex obtained by said antigen-antibody reaction and the conditions thereof are not particularly restricted but may be those in routine use for immunoassays in general.

Preferably the present invention can be carried into practice by the sandwich method. In the solid phase sandwich method, for instance, the target antibody in a sample can be assayed typically by the following procedure.

First, an $E.\ coli$ component and a sample supposedly containing the target antigen (a body fluid such as urine) are added to a solid phase antigen which is an immobilized antigen capable of undergoing a specific antigen-antibody reaction with the target antibody to thereby carry out an antigen-antibody reaction. After the unbound substances not coupled to the solid phase antigen are removed by washing, for instance, an antibody assay reagent is added for reaction with the target antibody coupled to the solid phase antigen (antigen-antibody complex) and the antigen-antibody complex is detected or quantitated by a detection means corresponding to the particular assay reagent.

The selection and modification of various means for such assays are well known to those skilled in the art and any of such techniques can be utilized in the practice of the present invention [e.g. "Rinsho Kensa-hou Teiyo (Outline of Clinical Test)", Kanehara Publishing Co., 1995].

The antibody assay reagent for use here is not particularly restricted but includes a variety of reagents in routine use in the art. For example, secondary antibodies such as an anti-human immunoglobulin antibody capable of binding the objective antibody (immunoglobulin) can be mentioned. The anti-human immunoglobulin antibody mentioned above includes the antisera, purified products thereof (polyclonal antibodies) and monoclonal antibodies available from arbitrary animals immunized using an immunoglobulin in the class corresponding to the target immunoglobulin as an immunogen.

Further, as the antibody assay reagent, an anti-IgG antibody having a specific affinity for the Fc region of the target antibody (IgG) can also be used. As such an anti-IgG antibody, an Fc-specific anti-IgG antibody which is not reactive to the light chain of IgG or the F(ab) region of IgG or protein A, protein G or the like which is specifically reactive to the Fc region of IgG can also be used. These can be used with particular advantage when the target antibody is an IgG.

Those antibody assay reagents can be prepared in the conventional manner or purchased from commercial sources.

For detection, the antibody assay reagent may be directly modified with a conventional labeling agent or indirectly modified by an additional detection means.

The labeling agent is not particularly restricted but any of the agents hitherto-known or expected to come into use in future can be employed. To mention specific examples, radioisotopes such as $^{125}I$, $^{3}H$, $^{14}C$, etc.; enzymes such as alkaline phosphatase (ALP), peroxidase (e.g. HRP), etc.; fluorescent substances such as fluorescein isothiocyanate (FITC), tetramethylrhodamine isothiocyanate (RITC), etc.; 1N-(2,2,6,6-tetramethyl-1-oxyl-4-piperidyl)-5N-(aspartate)-2,4-dinitrobenzene (TOPA), etc. can be used. The immunoassay methods using the above-mentioned labeling agents are called radioimmunoassay, enzyme immunoassay, fluoroimmunoassay, and spin immunoassay, respectively. The immunochromatoassay method using an antibody assay reagent prepared by labeling colloidal gold-stained latex particles can also be employed.

Labeling with those labeling agents, modifications by indirect labeling, and their detection can be made by the per se known methods [Tatsuo Iwasaki et al.: Monoclonal Antibody, Kodansha Scientific, 1984; and Eiji Ishikawa et al.: Enzyme Immunoassay, 2nd Edition, Igaku Shoin, 1982, among others].

In the assay method of the invention, it is essential that an *E. coli* component be included in the reaction system comprising the target antibody to be assayed and the corresponding antigen and as far as this requirement is satisfied, the rest of the basal procedure is not particularly restricted but may be the same as that used in conventional immunoassays or routinely in the art. Therefore, the conditions of the reaction between said antigen-antibody complex and said antibody assay reagent are not particularly restricted, either, but may be the same as those used in immunoassays in general. The commonest procedure comprises incubating or allowing to stand the assay system under the same conditions as those described above for the antigen-antibody reaction, i.e. generally at a temperature not over 45° C., preferably about 4~40° C., more preferably about 25~40° C. and a pH level of about 5~9 for about 0.5~40 hours, preferably about 1~20 hours.

The presence or absence of the target antibody in a sample or its content is evaluated by measuring the label activity, which depends on the kind of labeling agent used in the labeling of the antibody assay reagent (or the indirect label), in the routine manner or in terms of the antibody titer calculated from the measured value.

(1-2) As an alternative mode of the antibody assay method of the present invention, there can be mentioned an immunological method for assay of the target antibody in a sample which comprises using a reagent having a specific affinity for the Fc region of the target antibody IgG as the antibody assay reagent.

In accordance with this method, the reaction between the nonspecific binding antibody component and the antibody assay reagent can be significantly suppressed so that the frequency of false positive tests can be decreased. Thus, this antibody assay method may be regarded as an improvement in the sandwich method for immunoassay of antibodies.

The antibody assay reagent of the invention is reactive to the target antibody (IgG) and, therefore, can be used for detection of the antibody and is characterized in that it is not reactive to the light chain of the target antibody IgG or the F(ab) region of the target IgG, that is to say it has a specific affinity for the Fc region of the target IgG.

More particularly, said antibody assay reagent may for example be an Fc-specific anti-IgG antibody which can be prepared by using the Fc region of the target antibody IgG as the immunogen, and includes antisera, purified products thereof (polyclonal antibodies) and monoclonal antibodies which can be obtained from arbitrary animals immunized with said immunogen. This reagent is not limited to such antibody preparations but may be protein A, protein G or the like which is specifically reactive to the Fc region of the antibody IgG.

Those antibody assay reagents can be prepared in the routine manner or purchased from commercial sources (e.g. Sigma, Cappel or Jackson Immuno Research Laboratories, Inc.).

For detection, the antibody assay reagent may be directly modified with a conventional labeling agent or indirectly modified by an additional detection means.

The kind of labeling agent, method for labeling, and method of detecting the label can be the same as those mentioned under (1-1).

The antibody assay method of the invention comprises the use of the above-mentioned antibody assay reagent as an essential feature thereof in the detection of the target antibody, i.e. the antigen-antibody complex, and as far as this requirement is met, the rest of the basal procedure may be liberally the same as that used in conventional immunoassays by the sandwich technique.

Basically, the antibody assay method of the present invention is carried into practice by reacting an antigen capable of reacting with the target antibody in a sample and detecting the target antibody bound to the antigen (antigen-antibody complex) with said antibody assay reagent.

The assay sample and the antigen may respectively the same as mentioned under (1-1), and as to the target antibody, too, the same antibodies as those mentioned under (1-1) can be used, provided that the antibody is an antibody IgG against the infection source. In the method of the present invention, the infection source may include *Escherichia coli*.

Where necessary, the antigen or antibody assay reagent in the present invention can be used as immobilized on an arbitrary solid phase. The solid phase for use and the method of immobilization may for example be the same as mentioned under (1-1).

The antigen-antibody reaction between the antigen and the target antibody is not particularly restricted but can be conducted under the conditions in routine use for conventional immunoassays. A typical procedure comprises incubating or allowing to stand a reaction system comprising the antigen and target antibody generally at a temperature of not over 45° C., preferably about 4~40° C., more preferably about 25~40° C. for about 0.5~40 hours, preferably about 1~20 hours.

Although it is not mandatory, an *E. coli* component may be caused to be present in the antigen-antibody reaction as mentioned under (1-1).

The resulting antigen-antibody complex is then washed and submitted to a step in which it is reacted with said specified antibody assay reagent. This reaction can be carried out under the same conditions as are generally used in, or substantially in the same manner as, the conventional immunoassays (sandwich assays). The solvent, for instance, is not particularly restricted provided that it does not interfere with the reaction, thus including but not limited to buffers at pH about 5~9, such as citrate buffer, phosphate buffer, tris buffer and acetate buffer, to mention just a few examples. The reaction time and reaction temperature are not particularly restricted, either, but may for example be the same as those mentioned for said antigen-antibody reaction.

The presence or absence of the target antibody in a sample or its content is evaluated by measuring the label activity, which depends on the kind of labeling agent used in the labeling of the antibody assay reagent (or the indirect label), in the routine manner or in terms of the antibody titer calculated from the measured value, just as mentioned under (1-1).

(2) Antibody Assay Device

The antibody assay device according to the second aspect of the invention is now described in detail.

The antibody assay device of the invention is an improved method by which the presence and/or quantity of the target antibody to be detected in a sample can be determined with good accuracy by a solid phase assay procedure.

More particularly, the antibody assay device of the invention is an assay device comprising a solid phase support having at least (a) a first region for contact with a sample and (b) a second region for reaction of the antibody in the sample as arranged in such a sequence that the sample is transported by capillary action from said first region to said second region, and a label means for detecting the result of reaction in said second region, characterized in that said (b) second region has (i) a test site where a ligand for the target antibody to be assayed is immobilized and (ii) a control site where a ligand for capturing an arbitrary antibody in the sample is immobilized.

The outstanding feature of the antibody assay device of the invention is that a control site independent of a test site is provided in the second region, which control site is such that, when a proper sample is applied and tested in a proper manner, it forms an indication representing a positive test in the presence of a label regardless of whether the target antibody is present or not in the sample while, when an improper sample is applied or a sample is tested in an improper manner, it forms an indication representing a negative test in the presence of a label regardless of whether the target antibody is present or not in the sample.

Thus, the control site in the second region of this device is a site giving an indication of whether the result (particularly the negative result) in the test site is a valid assay result regardless of the presence or absence of the target antibody in the sample. With the antibody assay device of the invention, thanks to the above construction, it is possible to determine, qualitatively and quantitatively, the antibody in the sample with high accuracy (high reliability) with a clear distinction between false negative and true negative results.

Furthermore, the antibody assay device of the invention may be so designed that the reaction of the target antibody in the test site is carried out in the presence of an *E. coli* component or so designed that a reagent having a specific affinity for the Fc region of the target antibody IgG is used as the antibody assay reagent for detecting the result of reaction in the test site. With the antibody assay device of the invention, thanks to the above-described construction, non-specific reactions are inhibited so that the incidence of a false positive test is significantly decreased, thus making it possible to determine, qualitatively and quantitatively, the target antibody in the sample with good accuracy and high sensitivity.

As the assay sample and target antibody for this antibody assay device of the invention, those mentioned under (1) may for example be employed.

The present invention first provides a solid phase support comprising at least a first region and a second region.

The first region is a zone where the sample applied comes into contact with the device and the second region is a zone where the antibody (the total antibody which may contain the target antibody) in the sample undergoes reaction and coupling in the ligand-receptor mode or in the antigen-antibody mode and the result of reaction is displayed in the presence of a label (reaction zone and evaluation zone). Those regions are arranged on a solid phase support in such a manner that the sample applied and coming into the first region is transported by capillary action from said first region to the second region. Preferably, said regions are so arranged that all or at least a portion of the sample coming into the first region travels, by capillary action, through a substantially planar layer of the solid phase support to the second region.

Optionally the solid phase support may have a third region downstreams of the second region, as a region which absorbs the sample (liquid) migrating, by capillary action, from the first region to the second region and further downstreams.

The preferred solid phase support is formed in the shape of a strip and said first and second regions are arranged on one and the same plane of the strip in such a manner that the sample applied travels, by capillary action, from a first band (first region) to a second band (second region) and optionally further to a third band (third region). While the preferred form of said solid phase support is a strip as mentioned above, any other shape or geometry can be employed as far as the functions expected of the solid phase support in the present invention can be implemented.

The solid phase support is capable of absorbing the sample (liquid) and, when wetted with the sample, allowing at least the antibody in the sample to travel, by capillary action, from the first region to the second region of the solid phase support and optionally further to the third region. Moreover, the solid phase support is preferably one that is capable of supporting and immobilizing a ligand which reacts with the antibody (inclusive of the target antibody) contained in the sample to capture the latter.

The proper solid phase support includes a variety of porous materials, e.g. polyethylene, glass fiber, cellulose, rayon, nylon, crosslinked dextran, various types of chromatograph paper, nitrocellulose, and filter paper.

The first region, second region and third region, for instance, of the solid phase support may respectively be constituted by the same or different members selected from among the above-mentioned materials, with the choice of materials depending on the roles and functions of the respective regions.

The first region of the solid phase support is preferably constituted by a porous material adapted to absorb the sample applied onto its surface and let it travel, by capillary action, to the second region. The porous material suited for the first region is not particularly restricted but generally polyethylene (for example POREX: Porex Technologies, Fairburn, Ga.), glass fiber, rayon, nylon, and cellulosic materials inclusive of paper can be used. The preferred material is a porous polyethylene or a cellulosic material such as filter paper.

The second region of the solid phase support is preferably constituted by a porous material which is capable of allowing the sample (liquid) to be wicked by capillary action from the first region to the second region and supporting a ligand for the antibody (inclusive of the target antibody) occurring in the sample in a condition not dislodged by capillary action. The porous material having such properties includes filter paper, chromatograph paper, glass fiber, crosslinked dextran, nylon, nitrocellulose, etc. The preferred material is nitrocellulose because the ligand can be easily immobilized thereon.

The second region is provided with a test site where a ligand adapted to specifically recognize the target antibody in the sample and capture it has been immobilized and a control site where a ligand adapted to recognize an arbitrary antibody in the sample and capture it has been immobilized. The control site is disposed away from the test site with a given interval therebetween, preferably downstreams in the direction of capillary flow, and it is preferably so arranged that both sites are contacted by the sample liquid front under the identical conditions.

The ligand for the test site is not particularly restricted provided that it will be specifically coupled to the target antibody to be assayed but is preferably an antigen which is specifically recognized and bound by the target antibody (antigen-antibody reaction). As the antigen mentioned just above, those antigens which are in routine use in the conventional serum antibody assay system can be liberally used. Those antigens may be the very pathogens such as viruses and bacteria but may also be substances containing antigenic determinant groups intrinsic to the respective pathogens. Thus, for example, the pathogens inactivated by heating or irradiation, the antigens obtained by extracting the pathogens with a surfactant or the like, and those antigens which are artificially prepared by chemical synthesis or recombinant DNA technology can be mentioned.

The ligand for the control site is not particularly restricted provided that it couples an arbitrary antibody in the sample but is preferably an antibody (anti-immunoglobulin antibody) which specifically recognizes and binds an arbitrary antibody in urine.

Those ligands are immobilized on the porous material in the test site and control site, respectively, so that they will not be dislodged from the respective sites by the capillary flow of the liquid sample. Thus, each ligand is bound to the corresponding site on the porous support so that it will not be caused to diffuse when the second region is wetted by the sample containing the target antibody but be retained stationary in the site without being transported to the third region of the solid phase support.

Immobilization of the ligands on said porous support can be achieved by the techniques well known to those skilled in the art, i.e. by physical bonding or chemical bonding.

Thus, for example, chemical bonding methods such as covalent bonding methods, e.g. diazo method, peptide method (acid amide derivative method, carboxyl chloride resin method, carbodiimide resin method, maleic anhydride derivative method, isocyanate derivative method, bromocyan activated polysaccharide method, cellulose carbonate derivative method, condensing reagent method, etc.), alkylation method, crosslinking agent coupling method (the method for coupling to a support using glutaraldehyde, hexamethylene isocyanate or the like as the crosslinking agent), Ugi reaction coupling method, etc.; ionic binding methods; and physical adsorption methods can be mentioned. When nitrocellulose is used as the porous support for the second region, said ligand can be conveniently immobilized by non-covalent bonding.

The amount of the ligand (antigen) for use in the test site of the second region is preferably in excess so that essentially all of the target antibody presumably present in the sample will be bound to the test site.

The amount of the ligand (anti-immunoglobulin antibody) for use in the control site of the second region is also preferably in excess so that essentially all of the arbitrary antibody (which may contain the target antibody) in the sample will be bound to the control site.

The coupling reaction between the target antibody and the ligand (particularly an antigen) in the test site is preferably carried out in the presence of an $E.\ coli$ component. The $E.\ coli$ component may be supplied to the reaction system by incorporating it in a dilution of the assay sample and applying the mixture to the first region or may be removably immobilized in the test site of the solid phase support upstreams of the test site (e.g. said first region or the tracer region to be described hereinafter). The $E.\ coli$ component is not particularly restricted provided that it is derived from $Escherichia\ coli$ as mentioned above. Thus, it may be the protein fraction, carbohydrate fraction or lipid fraction of the cells or a mixture of such fractions. The soluble fraction obtained by extraction of the cells or the lipopolysaccharide (LPS) fraction can be mentioned as a preferred example.

As the sample is applied to the first region, the sample migrates, by capillary action, to the second region where the target antibody in the sample is bound and fixed to the test site within the second region and, then, the remaining arbitrary antibody (inclusive of the residue of the target antibody which has not been bound to the test site) is bound and fixed to the control site downstreams of the test site.

The labeling means in the present invention is used to detect whether the target antibody and arbitrary antibody in the sample have been coupled and fixed to said test site and control site, respectively.

The labeling means may consist of a ligand for the antibody and a detectable label coupled to said ligand.

The ligand for the antibody is not particularly restricted as far as it is a molecule which recognizes and binds the antibody present in the sample but, in the present invention, is preferably one which binds not only the target antibody to be assayed but also the arbitrary antibody present in the sample. As an example of such ligand, there can be mentioned the same ligand as that mentioned for the control site, particularly the same anti-immunoglobulin antibody as that adopted as the ligand in the control site.

The anti-immunoglobulin antibody mentioned above includes antisera available from arbitrary animals immunized with a relevant immunoglobulin, e.g. a human immunoglobulin, as the immunogen, purification products thereof (polyclonal antibodies) and monoclonal antibodies.

The anti-immunoglobulin antibody as the ligand in the control site may optionally be an antibody directed to all classes of antibodies so that it may capture and detect the total antibody in the sample or be an antibody directed to a desired class of antibody such as immunoglobulin G (IgG). Preferably, the ligand is an anti-immunoglobulin antibody directed to antibodies in the same class as the class to which the target antibody belongs and this arrangement is preferred in that as antibodies of the same class as the target antibody are thus detected in the control site, the optimum indication is obtained there for judging whether the assay has been done properly not only when a urine sample is used but when other body fluids such as sera are used as samples.

When the target antibody is IgG, the ligand as said labeling means is more preferably a ligand characterized by having a specific affinity for the Fc region of the antibody IgG and, as preferred examples of such ligand, an Fc-specific anti-IgG antibody which is not reactive to the light chain of the antibody IgG or the F(ab) region thereof or Protein A, Protein G or the like having a specific reactivity to the Fc region of the antibody IgG can be mentioned. Such anti-immunoglobulin antibodies or ligands can be prepared in the routine manner or purchased from commercial sources.

The detectable labeling component is not particularly restricted as far as it is a detectable label which is known to be useful for specific binding assays, particularly immunoassays, or which will be possibly used in the future [Tatsuo Iwasaki et al: Monoclonal Antibody, Kodansha Scientific, 1984; Eiji Ishikawa et al: Enzyme Immunoassay, 2nd Edition, Igaku Shoin, 1982, etc.].

The preferred label is one which undergoes change in color in the test site or control site of the second region. Though not restricted, a label undergoing a change of color which can be visually recognized without the aid of any instrument is particularly preferred. For example, various chromogens such as fluorescent substances and absorbing dyes can be mentioned. The still more preferred is a label in the form of a powder containing a visually detectable marker.

The suitable particulate label includes polymer particles (e.g. latex or polystyrene beads), sacks, liposomes, metallic gels (e.g. colloidal silver, colloidal gold, etc.), and polystyrene dye particles. Among them, metal gels such as colloidal silver and colloidal gold are preferred.

While such a label can be coupled to a ligand, either chemically or physically, in the conventional manner to provide a labeled ligand, commercial products can also be utilized.

The labeling means which can be used in the present invention may be any label that, when applied to the second region (inclusive of the test site and control site) of the solid phase support, indicates the result of the reaction with the antibody occurring in the sample which has taken place in the second region and, as far as this function can be achieved, there is no particular limitation on the mode of its presence. For example, when the assay device of the present invention is provided in the form of a flow through device, the labeling means may be included in the antibody assay reagent kit independently of the solid phase support.

Preferably, the labeling means is removably immobilized on a solid phase support, and more preferably it is removably immobilized upstreams of the second region of the solid phase support. The still more preferred mode is such that the labeling means is supported in a region (hereinafter referred to as tracer region) intermediate between the first and second regions of the solid phase support. In this mode of use, the sample applied to the first region is wicked by capillary action to the tracer region where it comes into contact with the labeled ligand to form the target antibody/labeled ligand complex and the arbitrary antibody/labeled ligand complex. After passage through the tracer region, the sample containing those complexes migrates, by capillary action, further to the second region. The ligand (antigen) disposed in the test site within the second region is specific to the target antibody and the ligand (anti-immunoglobulin antibody) disposed in the control site is specific to the arbitrary antibody. Therefore, the target antibody/labeled ligand complex which has migrated by capillary action is first captured in the test site and the remaining arbitrary antibody/labeled ligand-complex (inclusive of the target antibody/labeled ligand complex) in the sample is then captured in the control site.

The tracer region of the solid phase support is not particularly restricted as far as it is a support capable of transporting the test sample containing the target antibody and arbitrary antibody from the first region to the second region and supporting said labeled ligand in such a manner that the latter may be released by the capillary flow. Generally, it is a porous member made of polyethylene, glass fiber, rayon, nylon or a cellulosic material inclusive of paper. The preferred is a material which hardly allows nonspecific adsorption, for example glass fiber optionally treated with polyvinyl alcohol (PVA).

Among preferred embodiments of the invention is an embodiment wherein said tracer region and said test site in the second region are disposed with a given interval therebetween on a solid phase support. As such an interval region is provided between the tracer region and the test site, the antibody in the sample coming into contact with the labeled ligand in the tracer region is blended with the labeled ligand there before the sample reaches the test site in the second region, whereby the coupling reaction between the antibody and the labeled ligand is more positively assured. Thus, this region provides an incubation environment (time and space) for the coupling of the target antibody and arbitrary antibody with the labeled ligands prior to contact of the target antibody and arbitrary antibody in the sample with the test site and control site, respectively.

Furthermore, the solid phase support of the present invention may have a third region downstreams of the second region.

The sample continues migrating from the first region to the optional tracer region to the second region and further to the third region by capillary action. Thus, the third region functions as a region receiving the liquid coming from the second region by capillary action.

Generally the third region need only discharge the function of receiving the liquid component not bound in the second region but may be further provided with a site informative of the completion of an assay upon advance of the capillary flow of the sample (that is the liquid front) to a predetermined end-point zone on the solid phase support.

For the above purpose, the solid phase support may be provided with a visible indicator zone containing a water-soluble dye such as erythrosine B, saffranine O, phenol red or the like downstreams of the second region. In this case, as the liquid front of the sample traverses the second region into the third region, it flows through said indicator zone and the dye disposed in this zone is carried downstreams by the capillary flow of the sample (liquid), thereby informing that the sample has already passed serially through the first region, tracer region and second region (test and control sites) and accordingly that the assay has just been completed.

The material for the third region is not particularly restricted as far as it is capable of absorbing the sample (liquid), thus including porous films or sheets of polyethylene, rayon, nylon and cellulosic materials inclusive of paper. The preferred material is a cellulosic material such as paper.

The present invention is now described in detail, reference being had to the accompanying drawings showing the antibody assay device and its constituent members. It should, however, be understood that the illustrated device is a mere embodiment of the invention and by no means definitive of the invention.

FIG. 1 is a diagram showing a solid phase support in the form of a strip (60×5 mm) as a member of the device of the invention. In FIG. 1, the code 1 represents a first region (16×5 mm, 0.92 mm thick) where an assay sample is applied and brought into contact with the strip; the code 2 represents a tracer region (5×5 mm, 0.79 mm thick) where a labeled ligand (e.g. colloidal gold-labeled human IgG antibody) is immobilized; the code 3 represents a second region (18 mm×5 mm, 0.1 mm thick) where the reaction with the antibody in the sample takes place and the result is indicated; and the code 4 represents a third region (22×5 mm, 1.46 mm thick) where the sample which has migrated from the first region and second region is absorbed.

The thickness of the first region is generally 0.2~2 mm and preferably 0.8~1.2 mm, and the thickness of the tracer region is generally 0.2~1.5 mm and preferably 0.5~1 mm. The thickness of the second region is generally 0.03~0.2 mm and preferably 0.08~0.12 mm, and the thickness of the third region is generally 0.5~3 mm and preferably 1~2 mm. However, these ranges are not critical.

Disposed within said second region (3) is a test site (test line, about 1×5 mm) (5) where a ligand having a specific affinity for the target antibody is supported in position and a control site (control line, about 1×5 mm) (6) where a ligand having an affinity for the arbitrary antibody (anti-human immunoglobulin antibody) is supported in position. The test site (5) is disposed at a given distance (about 6 mm) from the tracer region and the control site (6) is disposed at a given distance (about 6 mm) from the test site (5). The test site has the function of reacting specifically with the target antibody in the sample and indicating in the presence of a label whether the target antibody exists or not in the sample and the control site has the function of indicating in the presence of a label whether the sample applied is proper or not.

The materials (supports) for the first region, tracer region, second region and third region constituting the solid phase support strip may have been simply connected in series in the longitudinal direction of the strip along which the sample migrates and there is no restriction to the mode of connection. Preferably, however, the connection between the longitudinally front end of the first region and the rear end of the tracer region, the connection between the front end of the tracer region and the rear end of the second region, and the connection between the front end of the second region and the rear end of the third region are respectively in superimposed relation. More preferably, as illustrated in FIG. 1, the longitudinally front end part of the first region is superimposed on the rear end part of the tracer region and the longitudinally front end part of the tracer region is superimposed on the rear end part of the second region. The rear end part of the third region may be superimposed on the front end part of the second region. In such a mode of connection, the sample applied to the first region is allowed to migrate smoothly in the longitudinal direction of the strip. The width of the strip in its longitudinal direction is not particularly restricted but may for example be 0.5~10 mm, preferably 1~2 mm, more preferably 0.8~1.2 mm. It should be understood that the top/bottom relationships of the respective regions in the superimposed strip structure are not limited to those mentioned above but may be reversed.

For convenience in use, the above solid phase support is preferably packaged in the form of an assay unit.

The principle of assay with the assay device of the invention is now explained with reference to FIG. 2.

(3) Solid Phase Assay Method

The third aspect of the invention is directed to a solid phase assay method using the above-described device, which specifically is a solid phase method for assay of the target antibody in a sample which comprises bringing the sample into contact with the first region of the antibody assay device and detecting the development of a color in the test site of the second region under the condition in which the control site of the second region is indicating a color.

In this assay, a sample suspected to contain the target antibody is first applied to the first region (1) of the solid phase support.

For application of the sample, a body fluid such as urine may be used as it is or after dilution with a suitable diluent. The diluent is not particularly restricted but includes various buffers having a buffer action within the range of pH about 5~9, preferably about 6.5~8.5, (e.g. citrate buffer, phosphate buffer, tris buffer, acetate buffer, borate buffer, etc.), surfactants, etc.

Since nonspecific reactions in the antigen-antibody reaction can be suppressed to reduce the incidence of a false positive test by conducting the antigen-antibody reaction in the presence of an *E. coli* component, it is preferable to use a diluent containing such an *E. coli* component. The amount of the *E. coli* component (LPS) to be incorporated in the diluent is not particularly restricted but is preferably such that about 0.1~10 µg, preferably about 0.5~5 µg, of said component will be available per µg of the ligand (antigen) in the reaction system, i.e. the test site.

The amount of the *E. coli* component (LPS) to be incorporated in the sample may for example be generally not less than 5 µg/ml, preferably 5~100 µg/ml, more preferably 10~50 µg/ml. Although the use of an amount over 100 µg/ml is not prohibitive, the effect of the invention can be accomplished at the addition level of up to 100 µg/ml.

As the sample is applied to the first region (1), the first region 1 is wetted. The sample applied flows through the first region (1) into the tracer region (2) by capillary action and comes into contact and reacts with the labeled ligand (colloidal gold-labeled anti-human IgG antibody) removably supported in the tracer region.

When a suitable sample is used and the target antibody is contained in the sample, both the target antibody and arbitrary antibody contained in the sample are coupled to said labeled ligand in the tracer region (2) to form a target antibody/labeled ligand complex and an arbitrary antibody/labeled ligand complex, respectively. After passage of the same through the tracer region (2), the respective complexes or the labeled ligand not forming such complexes are transported together with the sample downstreams of the tracer region (2). In a preferred mode, the labeled ligand not forming a complex yet is given a sufficient time (space) for forming complexes as it travels with the antibody-containing sample from the tracer region (2) to the test site (5) of the second region (3) by capillary action. As the sample reaches the test site (5) in the second region, the target antibody/labeled ligand complex in the sample is coupled to the ligand supported in the test site (5) and immobilized in situ. The sample further migrates downstreams by capillary action to reach the control site (6) where the arbitrary antibody/labeled ligand complex is coupled to the ligand (anti-human immunoglobulin antibody) in that site and immobilized there. Then, by detecting the complexes immobilized in the test site (5) and control site (6) in the second region according to the label component of the labeled ligand, the assay result can be indicated as a positive test. In contrast, when a sample not containing the target antibody is applied, said target antibody/labeled ligand complex to be immobilized in the test site (5) is not formed so that the label is not detected in this test site (5) (a negative test).

In this connection, the negative test indication in the test site (5) includes both a negative (false negative) test due to a low concentration of the sample (i.e. a small total amount of antibody in the sample) and a negative (true negative) test due to the absence of the target antibody in the sample. These negative tests cannot be differentiated from each other according to the result in the test site (5) alone. However, in the case of a false negative test, said arbitrary antibody/labeled ligand complex to be immobilized in the control site (6) is not formed so that the control site gives a negative indication, while in the case of a true negative test, said arbitrary antibody/labeled ligand complex is formed so that the control site gives a positive indication. Therefore, according to whether the indication at the control site is negative or positive, it is possible to tell whether the negative result in the test site (5) is a false negative test or a true negative test. Furthermore, when a labeled ligand which has been deactivated is used or otherwise a proper assay is not performed in a proper system, the control site (6) gives a negative indication so that the finding of a false negative test owing to such causes can be prevented.

The sample liquid containing all the unbound antibodies, labeled ligands, etc. continues to migrate further downstreams of the second region (3) to the third region (4). Optionally an indicator zone may be provided and, in this case, the liquid front coveys the dye from the indicator zone to the end-point zone, thus indicating the passage of the liquid and dye through the third region and completion of the assay.

Figure 3:
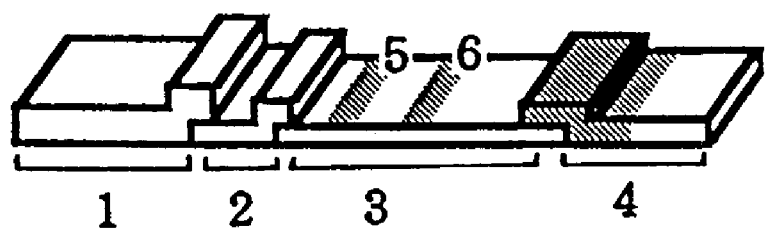
FIG. 3 is schematic diagrams showing a strip of solid phase support (A) and a housing (B) accommodating said solid phase support included in the antibody assay device of the invention.
Figure 3:
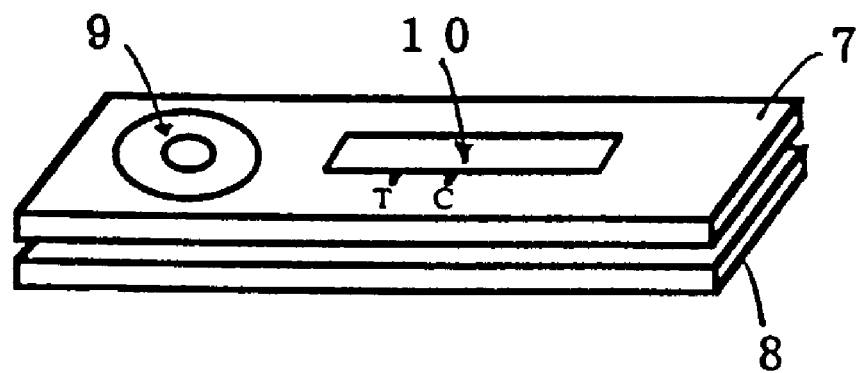

FIG. 3 shows an example of the antibody assay device of the invention for use in horizontal position. The solid phase support (A) comprising the first region (1), tracer region (2), second region (3) (including the test site (5) and control site (6)) and third region (4) is accommodated in a housing (B) made of a suitable material. The housing material is preferably a moldable plastic material such as polystyrene, although other materials such as glass, metal and paper can also be used. The housing consists of an upper section (7) having several apertures and a lower section (8), and the solid phase support is disposed on the lower section of the housing and covered with the upper section on top thereof. The apertures (9) and (10) in the upper section of the housing are disposed in alignment with the series of regions of the solid phase support and in the positions corresponding to the first region (1) and second region (3), respectively, of the solid phase support.

The sample can be applied to the first region (1) of the support from the aperture (9) (sample feeding port). The aperture (9) is preferably provided with a projecting peripheral wall around it so that the wall may assist in the dripping of the liquid sample onto the first region of the support. The method for contacting the sample with the first region of the solid phase support is not particularly restricted but the sample is preferably dripped from said sample feeding port perpendicularly to the plane of the solid phase support.

The aperture (10) is disposed in a position permitting a visual access to the test and control sites in the second region of the solid phase support, whereby the fixation of the labeled ligand/target antibody complex in the test site and that of the labeled ligand/arbitrary antibody complex in the control site can be visually confirmed (detection port, evaluation port). The aperture (10) need not necessarily be a single port permitting a visual access to both the test site and control site but may comprise two independent ports for the test site and the control site, respectively.

With the antibody assay device of the present invention, the presence or absence of the target antibody in a sample as well as the amount of the antibody can be determined with high accuracy by leaving the assay system standing for a few minutes to 30 minutes, preferably 5~20 minutes, after application of the sample, generally at a temperature of not over 45° C., preferably 4~40° C., more preferably about 15~30° C.

(4) Antibody Assay Reagent Kit

The antibody assay method described under (1) or the slid-phase assay method using the antibody assay device described under (2) can be more expediently carried out when an antibody assay reagent kit containing a complete set of various reagents and equipment necessary for determination of the antibody is utilized.

The present invention, thus, further provides an antibody assay reagent kit for reducing to practice said antibody assay method and said solid phase assay method.

The antibody assay reagent kit according to the present invention is intended for use for the purpose of detecting and quantitating an antibody in a sample through an antigen-antibody reaction and, as one preferred mode, includes a kit containing said *E. coli* component as a kit component. This reagent kit further contains an optionally immobilized antigen adapted to undergo antigen-antibody reaction with a target antibody to be assayed, an antibody assay reagent, and so forth. Furthermore, for convenience in assaying, this reagent kit may further include a suitable reaction medium, diluent, wash buffer, reaction stopper and/or label activity test reagent.

Moreover, as another mode, the antibody assay reagent kit of the invention may include a reagent having a specific affinity for the Fc region of the target antibody IgG, preferably an Fc-specific anti-IgG antibody.

As a further alternative mode, the antibody assay reagent kit of the invention may contain said antibody assay device. The reagent kit may further contain said *E. coli* component or said substance having a specific affinity for the Fc region of the target antibody IgG or both as reagents. Moreover, the kit may further contain such accessories as a pipette and an ampoule (tube) for use in dilution of the sample in addition to said reaction medium, diluent, wash buffer, reaction stopper, and label activity test reagent, among other reagents.

BEST MODE FOR CARRYING OUT THE INVENTION

The following examples are intended to illustrate the present invention in further detail and should by no means be construed as defining the technical scope of the invention. It should be understood that many changes and modifications may be made by those skilled in the art easily on the basis of the foregoing disclosure of the invention without departing from the technical scope of the invention.

EXAMPLE 1

Assay of *H. pylori*

(1) Preparation of *H. pylori* Antigen

*H. pylori* (a clinical isolate) was cultured on Brucella agar medium (Becton) for 48 hours (10% $CO_2$, 5% $O_2$, 37° C.) and the grown cells were harvested into cold PBS. The cells were centrifugally washed with cold PBS for a total of 5 times, and cold PBS was added so as to make a cell concentration of 100 mg/ml. Under stirring, one equivalent of cold 0.2% Triton X-100/PBS was added. The mixture was stirred for 5 minutes and centrifuged and the supernatant was recovered as *H. pylori* antigen solution and stored at −80° C.

(2) Preparation of an *H. pylori* Antigen Plate

The above *H. pylori* antigen solution (2.5 μg protein/ml) was added to a 96-well plate, 100 μl/well, and incubated at 4° C. overnight. After the wells were washed with PBS once, a blocking solution (Dulbecco-PBS [D-PBS], 1% BSA, 5% sorbitol, 0.05% $NaN_3$ [pH 7.4]) was added, 300 μl/well, and the plate was incubated at 4° C. overnight. After the blocking solution was discarded, the plate was dried at 25° C. overnight, sealed, together with a desiccant, in an aluminum bag and stored at 4° C. until used.

(3) Preparation of an *E. coli* Component

*Escherichia coli* (pvc18/JM109, Takara Shuzo) was cultured in ampicillin-containing liquid LB medium (Luria-Bertani medium, Nippon Seiyaku) at 37° C. for 18 hours. The culture was centrifuged to harvest the cells, which were washed with 2 portions of PBS. To the washed cells was added cold PBS to make 100 mg/ml, and the mixture was disrupted and extracted using a sonicator (10 seconds×3). The supernatant was recovered for use as an *E. coli* component and stored at −80° C. (hereinafter referred to as *E. coli* extract).

(4) Determination of Anti-*H. pylori* Antibody in Urine

Using urine as the sample, the anti-*H. pylori* antibody in the sample was determined.

To each well of the *H. pylori* antigen plate prepared under (2), 25 μl of a first buffer solution (200 mM Tris-HCl buffer, 0.14 M NaCl, 2% casein, 0.5% BSA, 0.05% Tween 20, 0.1% NaN$_3$ [pH 7.3]) containing 20 μg protein/ml of the *E. coli* extract and 100 μl of the urine sample were added. The mixture was stirred for 10 seconds and allowed to stand at 37° C. for 1 hour. The wells were washed with 6 portions of PBST (0.05% Tween 20 and 0.05% NaN$_3$ in PBS) and 100 μl of a 11,000-fold dilution of an enzyme (HRP)-labeled anti-human IgG antibody (peroxidase-conjugated Affini Pure Goat Anti-human IgG (Fc), Jackson Immuno Research) in a second buffer (50 mM Tris-HCl buffer, 0.14 M NaCl, 0.5% BSA, 5% goat serum, 0.05% Tween 20, 0.1% XL-II [pH 7.3]) was added. The plate was allowed to stand at 37° C. for 1 hour and, then, washed with 6 portions of PBST.

Then, 100 μl of a color developer solution (50 mM citrate-Na$_2$HPO$_4$, 50% TMB solution, 0.0075% H$_2$O$_2$) was added and reacted at room temperature for 20 minutes, at the end of which time 100 μl of a reaction stopper (50% TMB stop solution, 50% 1N-H$_2$SO$_4$) was added and the absorbance was measured.

(5) Results (i) In 5 cases of *H. pylori*-positive cases and the same number of *H. pylori*-negative cases as diagnosed by the $^{13}$C-UBT test [J. Gastroenterol., 33, pp.6-13, (1998)] which is regarded as the most accurate of all the diagnostic methods currently available for *H. pylori* infection, urine was sampled and the anti-*H. pylori* antibody in the urine was assayed by the procedure described under (4).

As a control experiment, the same procedure was applied to the same urine samples except that the addition of the *E. coli* extract was omitted and, based on the results, the effect of addition of an *E. coli* extract in accordance with the invention was evaluated.

The data are presented in FIG. 4.

In FIG. 4, the ordinate represents absorbance (O.D. 450~650 nm) and the abscissa represents the addition (+) or omission (−) of the *E. coli* extract. Furthermore, the open circles represent the results on urine samples from *H. pylori*-positive patients by the $^{13}$C-UBT test and the closed circles represent the results on urine samples from *H. pylori*-negative patients by the $^{13}$C-UBT test.

It will be apparent from FIG. 4 that by carrying out assays in the presence of an *E. coli* extract in accordance with this invention, *H. pylori*-positive and -negative cases could be clearly discriminated in agreement with the results of the $^{13}$C-UBT test, endorsing the high accuracy of the method of the invention.

Figure 5:
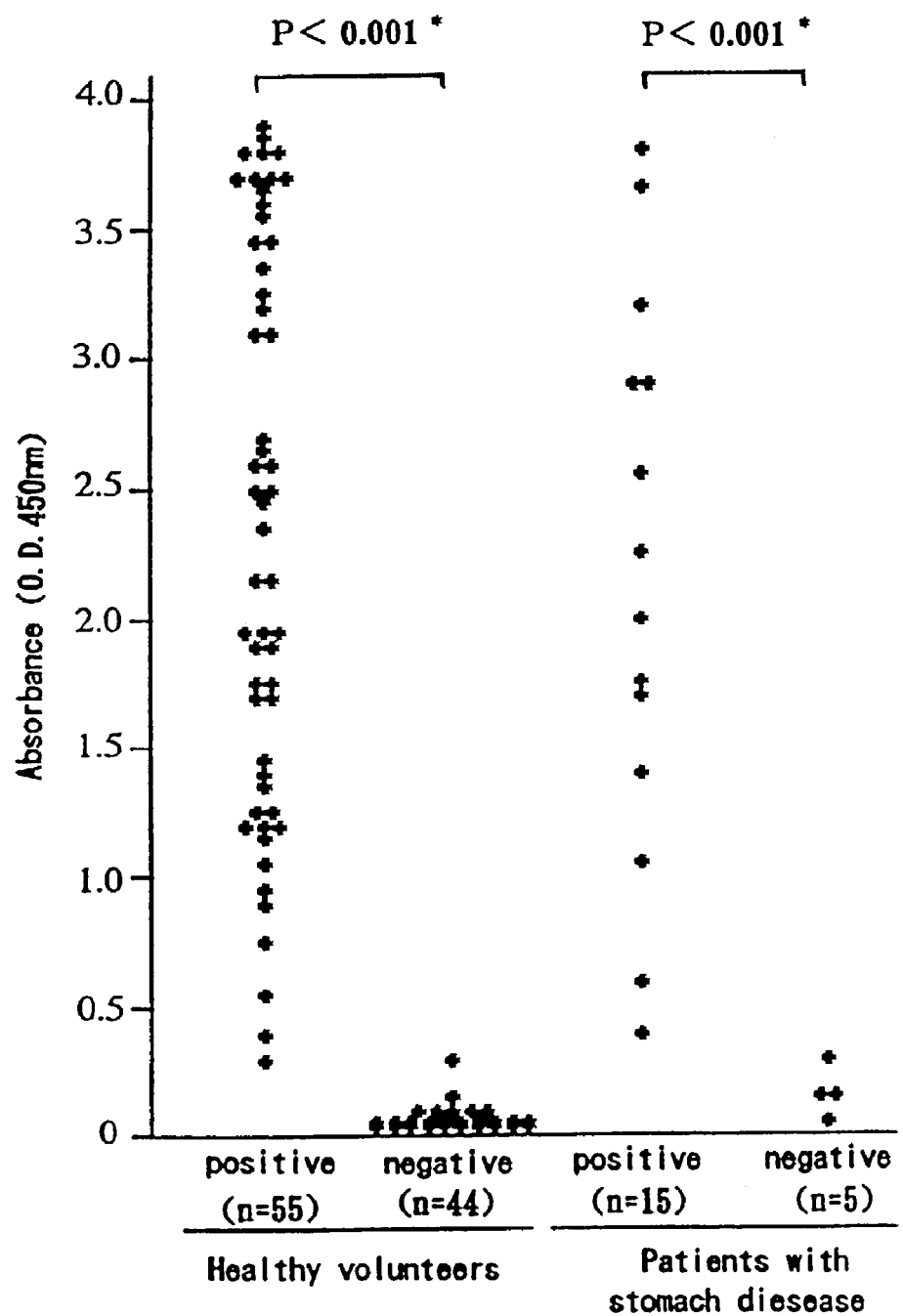
FIG. 5 is a diagrammatic representation of the data on anti-*H. pylori* antibody in urine as determined in Example 1 (5) (ii).

(ii) Using urine samples from 99 healthy volunteers having no history of an eradication treatment against *H. pylori* and 20 patients with stomach disease (7 cases of gastric ulcer and 13 cases of gastritis), the urinary anti-*H. pylori* antibody was assayed in the presence of the *E. coli* extract in accordance with the procedure described under (4). The results are presented in FIG. 5. In FIG. 5, the ordinate represents absorbance (O.D. 450 nm) and the abscissa represents the groups according to the $^{13}$C-UBt test (positive and negative cases). The results indicated that, in the assay system containing an *E. coli* extract, all urine samples from negative patients gave definitely negative results without a false positive result.

(iii) The amounts of anti-*H. pylori* antibody in sera from the same subjects as enrolled in the experiment (ii) were determined with commercial ELISA kits and the results were compared with the results of assays in urine by the method of the invention in the same subjects in regard of sensitivity, specificity and accuracy. The serum and urine samples from each subject were simultaneously collected and prepared for assays.

The commercial ELISA kits were as follows: HM-CAP™ kit, Enteric Products (HM-CAP); Helico G™ kit, Shield Diagnostic (Helico G); and HEL-p Test™ kit, Amrad Biotech (HEL-p). Each assay was performed in conformity with the protocol attached to each kit. The results are shown in Table 1.

TABLE 1

| Method of assay | Sample | Sensitivity | Specificity | Accuracy |
|---|---|---|---|---|
| HM-CAP | Serum | 80% (56/70) | 96% (47/49) | 87% (103/119) |
| Helico G | Serum | 99% (69/70) | 88% (43/49) | 94% (112/119) |
| HEL-p | Serum | 97% (68/70) | 90% (44/49) | 94% (112/119) |
| Method of invention | Urine | 99% (69/70) | 100% (49/49) | 99% (118/119) |

Referring to Table 1, "Sensitivity" means the positive rate generated with each kit in *H. pylori*-positive subjects (infection-positive according to $^{13}$C-UBT test: n=70), "Specificity" means the negative rate generated with each kit in *H. pylori*-negative subjects (infection-negative according to $^{13}$C-UBT test: n=49), and "Accuracy" means the percentage of accurate results with each kit in the total population (70+49=119 patients).

It is clear that despite the use of urine samples containing only trace amounts of the antibody, the determination of anti-*H. pylori* antibody by the method of the invention gave higher detection sensitivity and specificity as well as significantly higher accuracy as compared with the conventional blood antibody assay kits.

(6) Assay of Anti *H. pylori* Antibody in Urine

Figure 6:
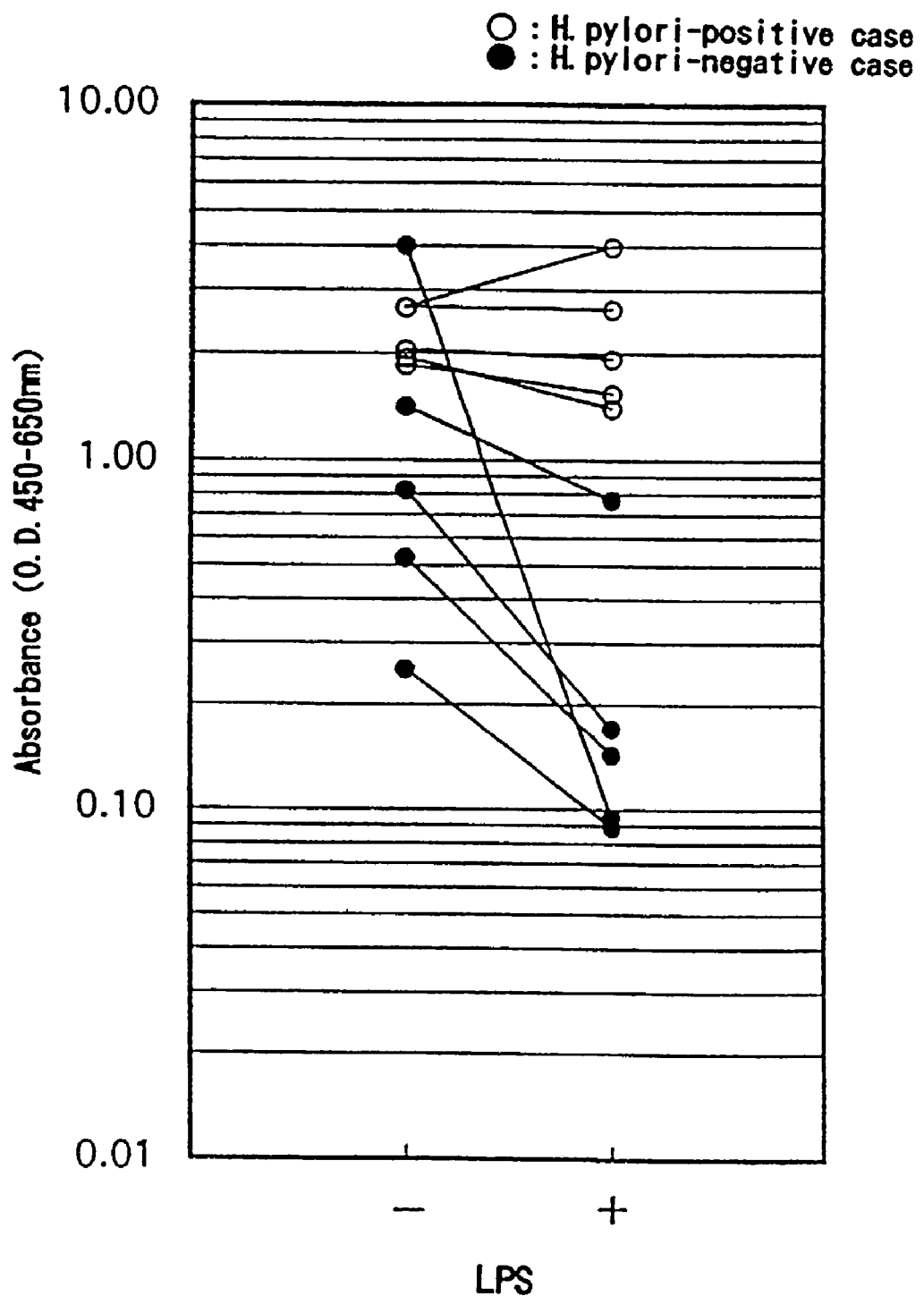
FIG. 6 is a diagrammatic representation of the data on anti-*H. pylori* antibody in urine as determined in Example 1 (6).

Using a first buffer containing *E. coli* LPS (Difco) (LPS concentration: 5 μg/well) in lieu of the *E. coli* extract, the procedure of (4) was otherwise repeated to determine the anti-*H. pylori* antibody in urine samples and the results were evaluated in the same manner as under (5) (i). The results are presented in FIG. 6. It is clear from the diagram that similar results can be obtained by using *E. coli* LPS in lieu of said *E. coli* extract.

EXAMPLE 2

Assay of Anti-Hepatitis B Virus (HBc) Antibody (1) Assay of Anti-hepatitis B Virus (HBc) Antibody An antigen plate was prepared using HBc antigen (Chemicon International) in accordance with the procedure of Example 1 (2) and the assay of anti-hepatitis B (core) (HBc) antibody in urine samples was carried out in accordance with Example 1 (4).

Thus, 25 μl of first buffer containing the *E. coli* extract in a varying concentration and 100 μl of sample urine were added to each well of the HBc antigen plate and after 10 seconds' stirring, the plate was allowed to sit at 37° C. for 1 hour. After the plate was washed with 6 portions of PBST, 100 μl of a 11,000-fold dilution of enzyme (HRP)-labeled anti-human IgG antibody in second buffer was added and the plate was allowed to sit at 37° C. for 1 hour and then washed (6 times with PBST).

Then, 100 μl of a color developer solution was added and the reaction was carried out at room temperature for 20 minutes, after which 100 μl of a reaction stop solution was added and the absorbance was measured.

(2) Results

In 5 positive and 5 negative blood anti-HBc antibody cases as classified by assays using a commercial anti-HBc antibody assay kit (Dinabott), the anti-HBc antibody in urine was determined by the procedure described under (1).

The concentrations of the *E. coli* extract in reaction mixtures were set at 0, 0.78, 1.56, 3.13, 6.25, and 12.5 μg/ml and the effect of addition of the extract was evaluated. The results are presented in FIG. 7.

Figure 7:
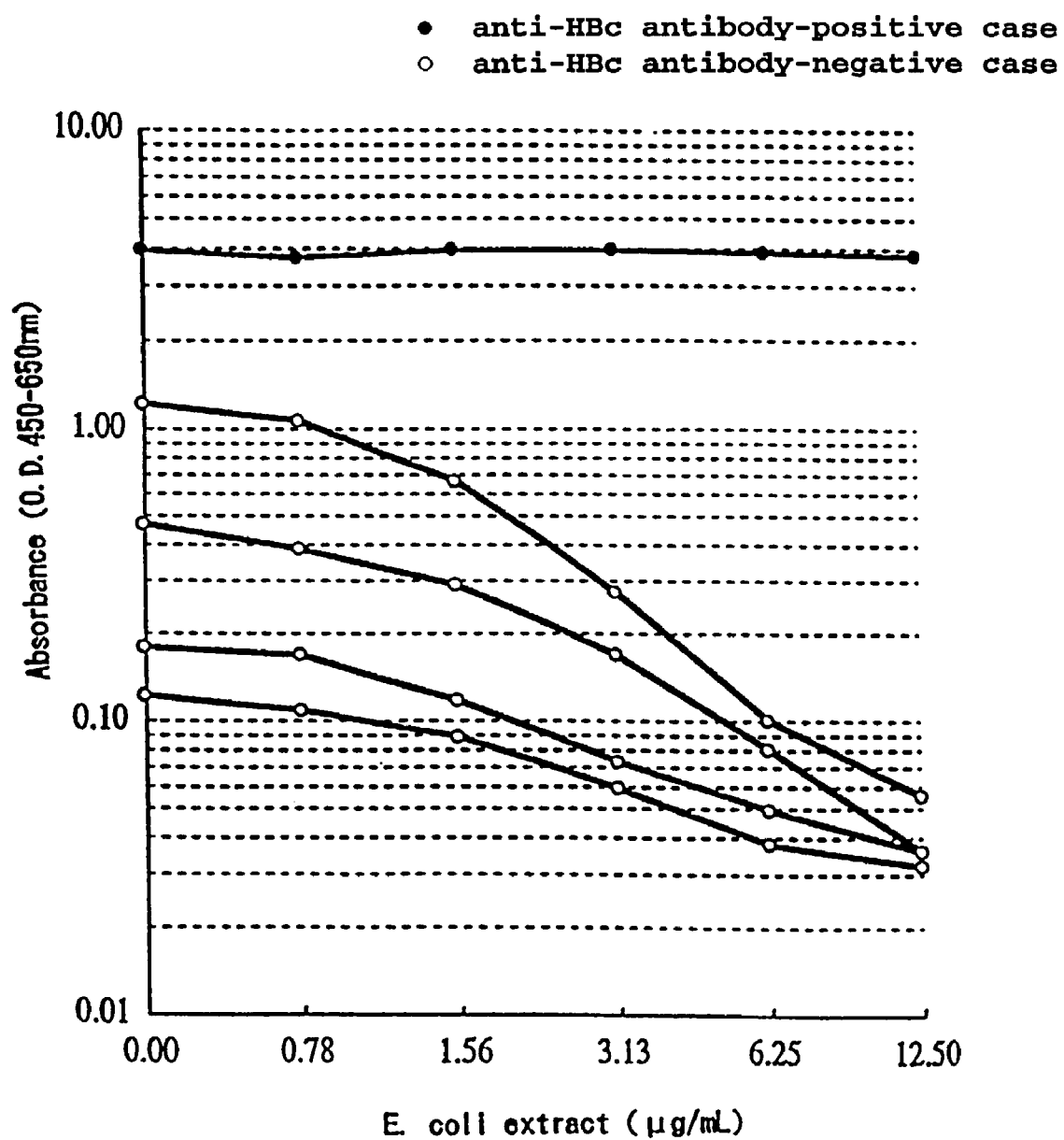
FIG. 7 is a diagrammatic representation of data on anti-HBc antibody in urine as generated in Example 2 (2).

In FIG. 7, the ordinate represents absorbance (O.D. 450~650 nm) and the abscissa represents the level of addition of the *E. coli* extract. Further, the closed circles represent data on the urinary antibody in patients with positive blood anti-HBc antibody and the open circles represent data on the urinary antibody in patients with negative blood anti-HBc antibody. It is apparent from the diagram that even when urine samples are used, the difference in the detection level of anti-HBc antibody between the group of patients with positive blood anti-HBc antibody and the group of those with negative blood anti-HBc antibody becomes more prominent in relation to the level of addition of the *E. coli* extract.

EXAMPLE 3

Using urine samples which gave false positive tests in the determination of anti-HIV antibody in urine by a known assay method [(Calypte™ HIV-1 Urine EIA: Arch. Pathol. Lab. Med., 119, 139-141 (1995); Clinical Infectious Diseases, 19, 1100-1104 (1994)], an exploratory experiment was carried out to identify the component supposedly responsible for a nonspecific reaction in the same assay system.

(1) Each of the above urine samples was adjusted to pH 7.4 with 1 M phosphate buffer (pH 7.7) and filtered through 5.0, 0.8 and 0.2 μm-cut filters. A 20 ml portion of the filtrate was concentrated by ultrafiltration (a 10 kDa-cut membrane) to 2 ml. The concentrated urine was subjected to gel permeation chromatography (Sephacryl S-300, Pharmacia) and each fraction was tested for its reactivity to HIV antigen.

The reactivity to HIV antigen was confirmed by causing each fraction to react with an HIV antigen-immobilized plate prepared by immobilizing HIV antigen (gp160) and detecting the conjugate (nonspecific binding component) with ALP-labeled goat anti-human (IgG+IgM) antibody, ALP-labeled goat anti-human IgG (Fc-specific) antibody or HRP-labeled goat anti-human IgG (Fab-specific) antibody (all available from Jackson ImmunoResearch Labs). The results are presented in FIG. 8.

Figure 8:
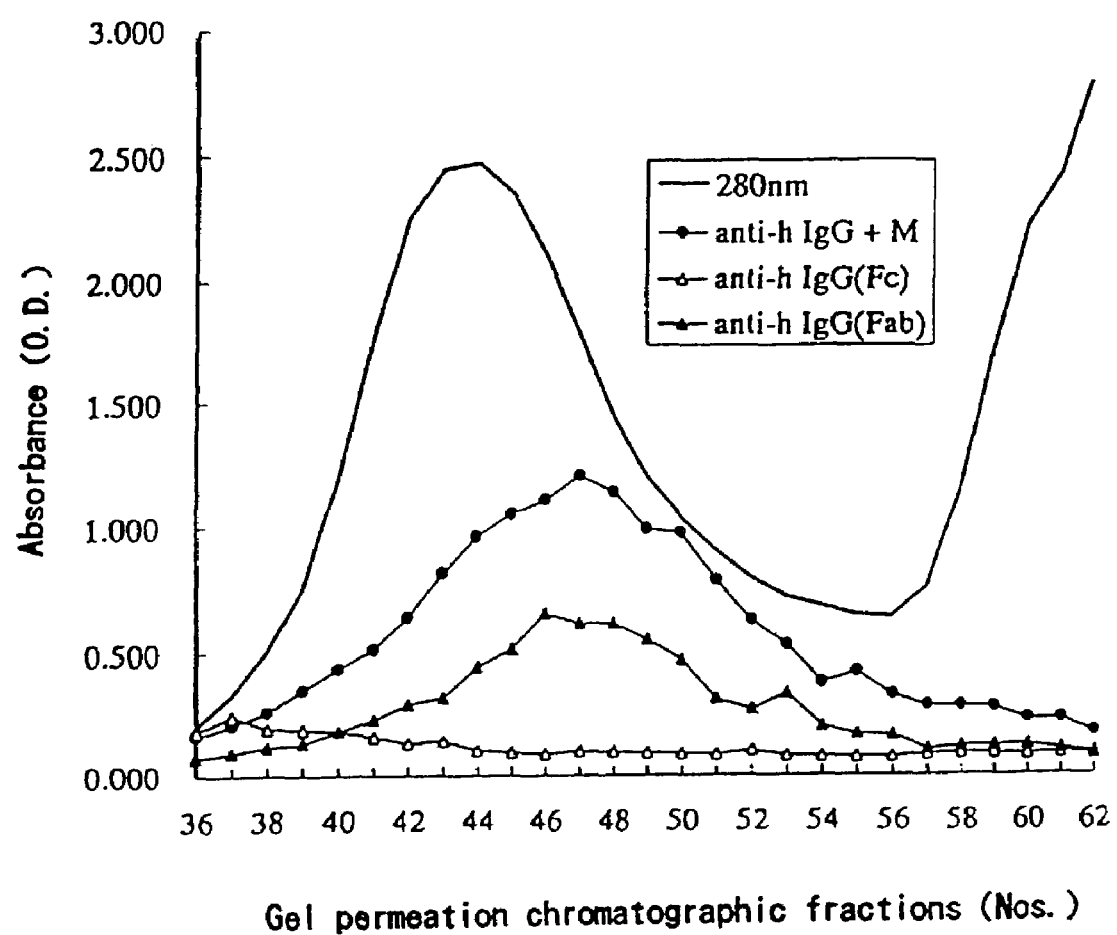
FIG. 8 is a diagram showing gel permeation chromatograms of urine samples giving false positive reactions in the determination of anti-HIV antibody in urine and the antibody reactivity of each fraction (Example 3 (1)).

In FIG. 8, the ordinate represents absorbance (O.D.) and the abscissa represents gel permeation chromatographic fractions (fraction Nos.). The solid line represents the absorbance of the protein at 280 nm and the closed circle-line represents the result of detection with said anti-human (IgG+IgM) antibody, the open triangle-line represents the result of detection with said anti-human IgG (Fc-specific) antibody, and the closed triangle-line represents the result of detection with said anti-human IgG (Fab-specific) antibody.

It is apparent from FIG. 8 that in the detection with anti-human IgG (Fab-specific) antibody, the mode of reaction (reactivity with the nonspecific binding component) is the same as in the detection with anti-human (IgG+IgM) antibody, while no reactivity is found with anti-human IgG (Fc-specific) antibody. This finding suggested that the nonspecific binding component is a fragment or denaturation product of human IgG which retains the reactivity with anti-human IgG (Fab-specific) antibody without Fc region.

Therefore, it was clear that when an anti-human IgG (Fc-specific) antibody not reactive to such nonspecific binding component is used as the assay reagent, the nonspecific reaction in the antibody detection system and, hence, the incidence of a false positive test due to such nonspecific reaction can be inhibited, with the result that a highly specific and very accurate antibody assay method can be provided.

EXAMPLE 4

Assay of Anti-HIV Antibody in Urine

To each well of an HIV antigen plate (Calypte™ HIV-I Urine EIA, Calypte Biomedical Corp.), 25 μl of first buffer (the sample buffer of Calypte™ HIV-I Urine EIA) and 200 μl of sample urine were added, and after 10 seconds' stirring, the plate was allowed to sit at 37° C. for 1 hour. After this plate was washed 6 times (wash buffer: D-PBS, 0.05% Tween 20), 100 μl of a 11,000-fold dilution of HRP-labeled goat anti-human IgG (Fc-specific) antibody (Peroxidase-conjugated Affini Pure Goat anti-Human IgG, Fc Fragment Specific, Jackson ImmunoResearch Labs.) in second buffer (50 mM Tris-HCl buffer, 0.14M NaCl, 0.5% BSA, 5% Goat Serum, 0.05% Tween 20, 0.1% XL-II (pH 7.3)) was added and the plate was allowed to sit at 37° C. for 1 hour and washed (6 times) in the same manner as above.

Then, 100 μl of a color developer (50% TMB solution, 50 mM Citrate-$Na_2HPO_4$, 0.0075% $H_2O_2$) was added and reacted at room temperature for 10 minutes, at the end of which time 100 μl of a reaction stop solution (50% TMB stopper, 50% 1N-$H_2SO_4$) was added and the absorbance (O.D. 450 nm) was measured.

As a control experiment, the sample was assayed with the known assay method [Calypte™ HIV-1 Urine EIA: Arch. Pathol. Lab. Med., 119, 139-141 (1995); Clinical Infectious Diseases, 19, 1100-1104 (1994)] (control method) using ALP-labeled goat anti-human immunoglobulin antibody as a second antibody. Furthermore, the negative control and positive control of the above assay kit were measured by the above assay method of the invention. Since the absorbance values thus found were comparable to those found with the above kit, the cut-off point for the method of the invention was set at the value found by adding 0.180 to the mean absorbance of the above negative control in accordance with the cut-off value calculation method of the same kit.

The results of assays in 100 samples (urine) from subjects with positive serum anti-HIV antibody (2 cases) and subjects with negative serum anti-HIV antibody (98 cases) are presented in Table 2.

TABLE 2

| | | Method of invention | | |
|---|---|---|---|---|
| | | Positive | Negative | Total |
| Control method | Positive | 4* | 26 | 30 |
| | Negative | 0 | 70 | 70 |
| | Total | 4 | 96 | 100 |

*Of these 4 subjects, 2 are subjects with positive serum anti-HIV antibody.

It can be seen from Table 2 that although both the sensitivity of the method of the invention and that of the control method were 100% (2/2), the specificity was 71.4% (70/98) for the control method vs. 98% (96/98) for the method of the invention.

The above results indicate that as compared with the control method, the antibody assay method of the invention is remarkably low in the incidence of a false positive test and very high in specificity.

EXAMPLE 5

Assay of Anti-*H. pylori* Antibody in Urine (1) Preparation of an *H. pylori* Antigen Plate To a 100 mg/ml suspension of *Helicobacter pylori* (a clinical isolate) in cold Dulbecco-PBS as prepared in the routine manner [J. Clin. Microbiol., 29: 2587-2589 (1991)], an equal volume of cold 0.2% Triton-X solution was added under constant stirring with a stirrer and the mixture was further stirred for 5 minutes and centrifuged (3,000 rpm, 20 min.). The supernatant was transferred to a new tube for use as the extract (1~1.5 mg/ml as protein).

This extract was diluted with D-PBS (2.5 µg/ml) and the dilution was distributed into a 96-well plate, 100 µl per well, and incubated at 25° C. overnight. After each well was washed, 300 µl of a blocking solution (D-PBS, 0.5% casein, 5% sorbitol, 0.05% $NaN_3$ (pH 7.4)) was added, followed by incubation at 25° C. overnight. The blocking solution was then discarded and the plate was dried at 25° C. overnight, sealed together with a desiccant in an aluminum bag and stored at 4° C. until used.

(2) Assays

Using the immobilized antigen (plate) prepared as above, anti-*H. pylori* antibody in urine samples was assayed as in Example 4.

Thus, 25 µl of first buffer (200 mM Tris-HCl buffer, 0.14 M NaCl, 2% casein, 0.5% BSA, 0.05% Tween 20, 0.1% $NaN_3$, 20 µg/ml *E. coli* extract (pH 7.3)) and 100 µl of sample urine was added to each well and after 10 seconds' stirring, the plate was allowed to sit at 37° C. for 1 hour and then washed 6 times. Just as in Example 4, 100 µl of said dilution of HRP-labeled goat anti-human IgG (Fc-specific) antibody in second buffer was added and the plate was allowed to sit at 37° C. for 1 hour to detect the antibody.

Figure 9:
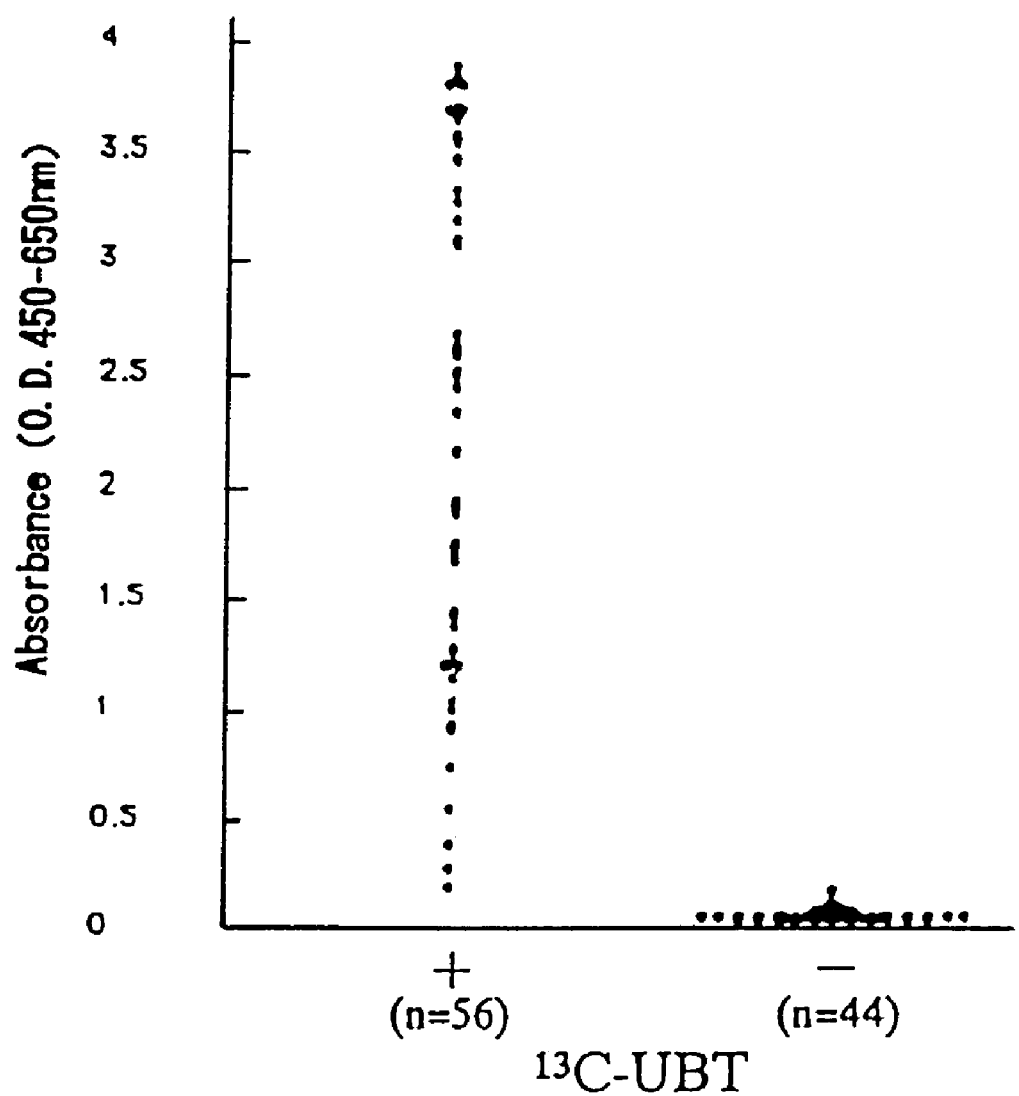
FIG. 9 is a diagrammatic representation of data on anti-*H. pylori* antibody in urine as determined in Example 5.

The results obtained are presented in FIG. 9 and Table 3.

TABLE 3

|  | Sample | Cut-off Point | Sensitivity $^{13}$C-UBT (+) | Specificity $^{13}$C-UBT (−) | Accuracy |
|---|---|---|---|---|---|
| Method of invention | Urine | M + 3SD (0.104) | 56/56 (100%) | 42/44 (95%) | 98% |
|  | Urine | M + 5SD (0.147) | 56/56 (100%) | 43/44 (98%) | 99% |
| Control method | Serum | M + 3SD (1.27) | 53/56 (95%) | 43/44 (98%) | 96% |
|  | Serum | M + 5SD (1.82) | 47/56 (84%) | 43/44 (98%) | 90% |

In FIG. 9, the ordinate represents absorbance (O.D. 450~650 nm) and the abscissa represents the positive *H. pylori* infection group (+; n=56) and negative *H. pylori* infection group (−; n=44) according to the $^{13}$C-UBT test [J. Gastroenterol., 33: pp. 6-13 (1998)].

In Table 3, "Sensitivity" denotes the percentage of cases detected as positive among the positive cases according to $^{13}$C-UBT test; "Specificity" denotes the percentage of cases detected as negative among the negative cases according to $^{13}$C-UBT test; and "Accuracy" denotes the percentage of cases detected as positive and negative, respectively, among the positive and negative cases according to $^{13}$C-UBT test, the respective figures corresponding to the cut-off point of mean M+3SD or M+5SD. As a control experiment, the same urine samples were assayed with a serum anti-*H. pylori* antibody assay kit [HM-CAP; EPI/Kyowa Medics (K. K.)] and the results are also tabulated (Control method).

The above results indicate that the method of the invention is superior to the control method in sensitivity and accuracy in particular.

Example 6

Assay of Anti-rubella Virus Antibody in Urine (1) Preparation of a Rubella Antigen Plate Using a commercial rubella antigen [available from BIO-DESIGN] in a concentration of 1 µg/ml and a blocking agent composed of D-PBS, 1% BSA, 5% sorbitol and 0.05% NaN, (pH 7.4), the procedure of Example 5 (1) was otherwise repeated to provide a rubella antigen plate.

(2) Assays

Using the above antigen plate, the rubella antibody in urine samples was assayed in the same manner as in Example 5 (2). The results are presented in FIG. 10 and Table 4.

TABLE 4

|  |  | Control method (serum ELISA) | | |
|---|---|---|---|---|
|  |  | Positive | Negative | Total |
| Method of invention (urine ELISA) | Positive | 76 | 0 | 76 |
|  | Negative | 0 | 23 | 23 |
|  | Total | 76 | 23 | 99 |

Figure 10:
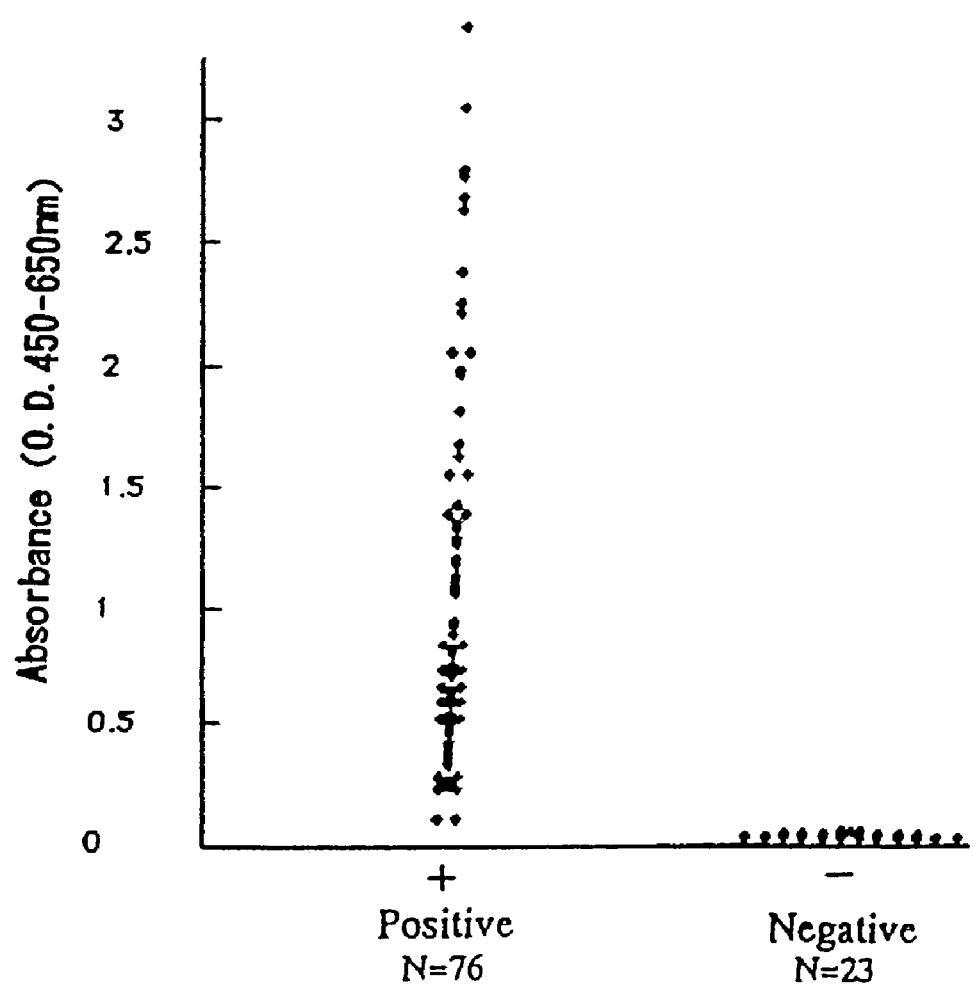
FIG. 10 is a diagrammatic representation of data on anti-rubella antibody in urine as generated in Example 6.

In FIG. 10, the ordinate represents absorbance (O.D. 450~650 nm) and the abscissa represents the serum anti-rubella antibody-positive group (n=76) and -negative group (n=23) according to the results of determination with a commercial kit (Rubella IgG (II)-EIA, SEIKEN; available from Denka Seiken). The data given in Table 4 indicates a complete agreement between the result obtained in urine by the method of the invention and the result obtained in sera by the control method.

According to the above data, the degree of agreement between the method of the invention and the control method is as high as 100% (99/99), thus indicating that the invention enables detection of the antibody with high sensitivity and high specificity even in urine which is safe and convenient and is, therefore, of great use in the laboratory examination.

EXAMPLE 7

Construction of an Antibody Assay Device (1) Preparation of an *H. pylori* Antigen An *H. pylori* antigen solution was prepared by the same procedure as in Example 1 (1) and stored at −80° C.

(2) Preparation of a Labeled Anti-human IgG Antibody-containing Dry Glass Fiber

To a glass fiber sheet (5.0 mm ×260 mm ×0.8 mm thick; Whatman) was added 1 ml of a 40 nm (dia.) colloidal gold-labeled anti-human IgG (Fc-specific) antibody solution and the sheet was dried overnight. This sheet was stored together with a desiccant at room temperature until used.

(3) Preparation of a Membrane

Figure 11:
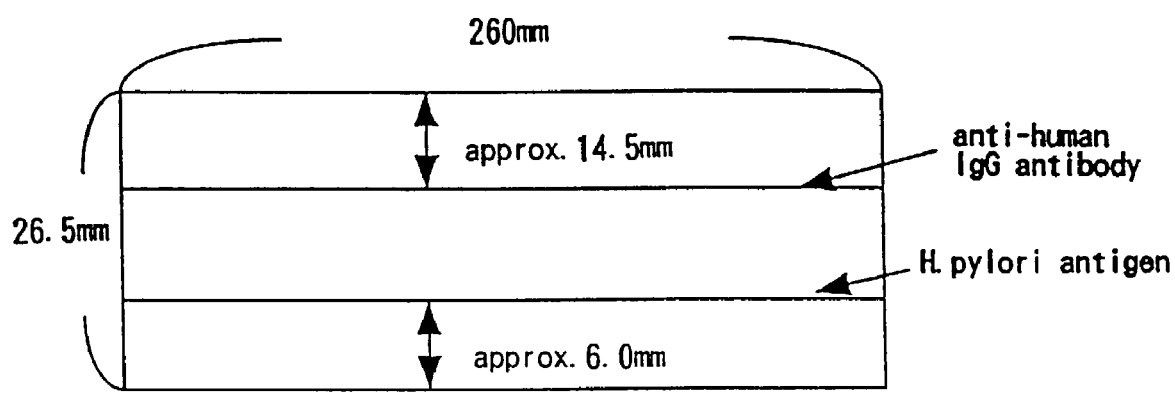
FIG. 11 is a diagram showing the test site and control site in the second region of the antibody assay device of the invention [Example 7 (3)].

The *H. pylori* antigen solution (3 mg/ml) prepared under (1) above and an anti-human IgG antibody solution (0.3 mg/ml) were respectively applied onto a nitrocellulose membrane (26.5 mm×260 mm×0.1 mm thick; Advance MicroDevice) by spraying (1.5 μl/cm) in lines at a predetermined spacing as illustrated in FIG. 11 and dried at 37° C. for 120 minutes. After drying, the membrane was dipped and washed in a skim milk-containing Borax Buffer (pH 8.2) for 30 minutes. The washed membrane was dried at 37° C. for 1 hour and stored in the presence of a desiccant at room temperature.

(4) Assembly (a Solid-phase Support)

As illustrated in FIG. 3(A), the above membrane (3), an absorbent filter paper pad (4) (22×260 mm×1.5 mm thick; Whatman), said labeled antibody-containing glass fiber sheet (2) and a sample pad (1) (15×260 mm×1.0 mm thick; filter paper, Whatman) were glued together with an adhesive and cut to 5 mm in width.

The solid-phase support thus prepared was set in position on a bottom section (8) of a plastic housing and a top section (7) provided with a sample inlet port (9) and a detection window (10) in series was placed over the solid-phase support and set securely on the bottom section (8).

EXAMPLE 8

Assay of Anti-*H. pylori* Antibody in Urine

Using the device constructed in Example 7, the assay of anti-*H. pylori* antibody was carried out in 3 kinds of urine samples, namely samples of urine from subjects with *H. pylori* infection, samples of urine from subjects without *H. pylori* infection, and extremely lean samples of urine from subjects with *H. pylori* infection.

First, 500 μl of sample urine was added to 500 μl of a sample diluent [200 mM Tris-HCl buffer, 0.14M NaCl, 2% casein, 0.5% BSA, 0.05% Tween 20, 0.1% NaN3 (pH7.3), *E. coli* LPS (Difco) 50 μl /ml], followed by mixing. Six drops (about 150 μl) of the resulting dilution was dripped from the sample inlet port (9) of the device constructed in Example 7 for adsorption on the support which was then allowed to sit for 20 minutes. As a result, when a qualified urine sample was used, a pink~red color band appeared in the control region of the detection window (10). On the other hand, when an extremely lean unqualified urine sample was used, neither the test region nor the control region of the detection window (10) showed a color development, indicating that the sample was not evaluable. When the sample was a qualified urine sample from a subject without *H. pylori* infection, a pink~red color band appeared only in the control region of the detection window (10) showing a negative (true negative) test for *H. pylori* infection, while in the presence of *H. pylori* infection, a pink~red color band appeared in both the test region and control region of the detection window (10), showing a positive test for *H. pylori*.

EXAMPLE 9

Assay of Anti-*H. pylori* Antibody in Urine (1) Preparation of an *E. coli* Component

*Escherichia coli* (pvc18/JM109; Takara Shuzo) was cultured in ampicillin-containing liquid LB medium (Luria-Bertani medium; Nihon Seiyaku) at 37° C. for 18 hours and the grown cells were harvested by centrifugation and washed with 2 portions of PBS. Then, cold PBS was added at a final cell concentration of 100 mg/ml and the cells were disrupted and extracted using a sonicator (10 seconds×3 times). The resultant supernatant was used as *E. coli* extract protein.

(2) Using the *E. coli* extract protein prepared under (1) above in lieu of the *E. coli* LPS added to the sample diluent in Example 8, the procedure of Example 8 was otherwise repeated to determine anti-*H. pylori* antibodies in urine samples. As a result, the same results as described in Example 8 were obtained.

EXAMPLE 10

Using the whole blood, plasma and urine from 21 *H. pylori* infection-positive subjects and the same number of *H. pylori* infection-negative subjects (a total of 42 cases) according to the $^{13}$C-UBT test [J. Gastroenterol., 33:6-13 (1998)], anti-*H. pylori* antibodies in samples were assayed by the procedure described in Example 8.

As a control experiment, samples from the same subjects were respectively assayed using commercial *H. pylori* antibody assay kits directed to whole blood or plasma and the effectiveness of the device of the invention was evaluated from the data. The results are presented in FIG. 12.

Figure 12:
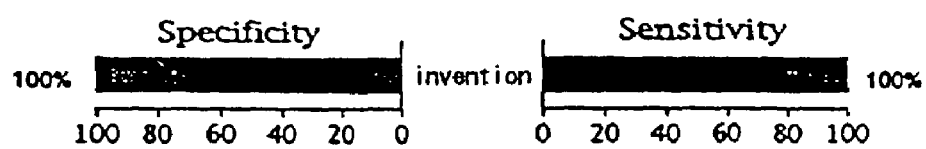
FIG. 12 is a histogram showing assay data on anti-*H. pylori* antibody in the urine, whole blood and plasma as generated with the antibody assay device of the invention in comparison with the corresponding data generated with control devices (A~E).
Figure 12:
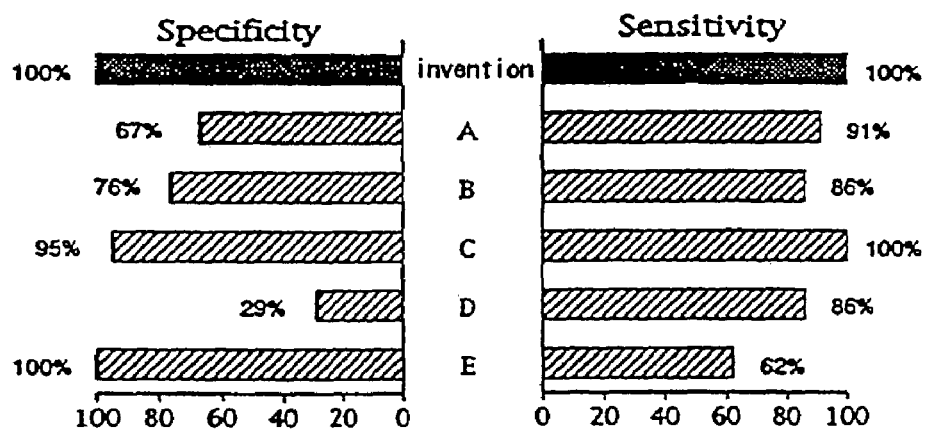
Figure 12:
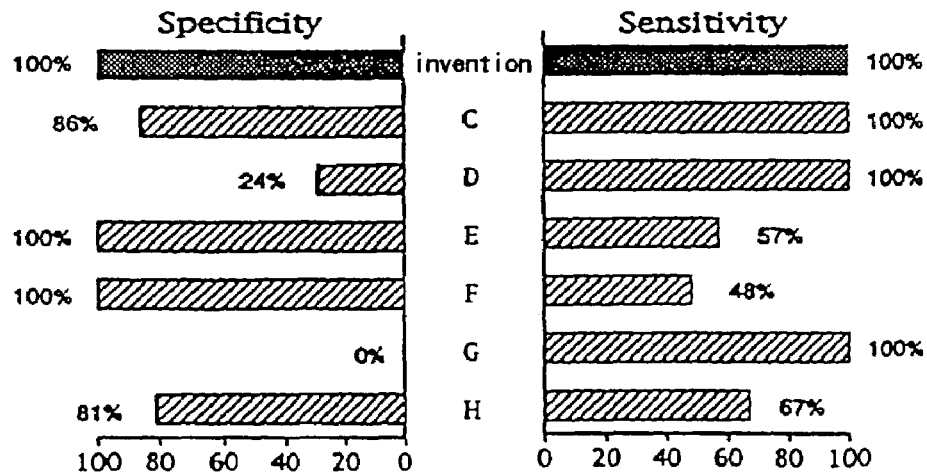

In FIG. 12, control kits A through H were as follows.

| | |
|---|---|
| A: | Helitest (manufactured by Cortecs Diagnostics) |
| B: | *H. pylori* -Check-1 |
| | (manufactured by Bio-Medical Products) |
| C: | First Check *H. pylori* |
| | (manufactured by Worldwide Medical Corp) |
| D: | Biocard *Helicobacter pylori* IgG |
| | (manufactured by Anti Biotech Oy) |
| E: | Insta Test *H. pylori* |
| | (manufactured by Cortez Diagnostics Inc.) |
| F: | One Step *H. pylori* Test |
| | (manufactured by Teco Diagnostics) |
| G: | *H. pylori* SPOT |
| | (manufactured by International Immuno-Diagnostics) |
| H: | Quick Stripe *H. pylori* |
| | (manufactured by Diatech Diagnostics Inc.) |

In FIG. 12, "Specificity" denotes the percentage of negative tests (negative rate) as found by assaying $^{13}$C-UBT test-negative samples with the corresponding kit, and "Sensitivity" denotes the percentage of positive tests (positive rate) as found by assaying $^{13}$C-UBT-positive samples with the corresponding kit.

It is apparent from the data in FIG. 12 that the antibody assay device and solid-phase assay method of the-present invention provide excellent assay systems with high detection specificity and accuracy even when applied to urine samples, not to speak of blood (whole blood, plasma) samples.

It is also clear from the above results that even when the sample is a urine sample which is safe and convenient, the present invention enables high-sensitivity, high-specificity detection of antibodies, thus being of great use in the laboratory examination.

EXAMPLE 11

Effect of an *E. coli* Component on the Assay of Antibodies in Urine (1) The effect of an *E. coli* component on the assay of antibodies in urine was evaluated using the assay device constructed in Example 8. Thus, using the urine from *H. pylori* infection-positive and -negative subjects selected by the $^{13}$C-UBT test, anti-*H. pylori* antibodies in urine samples were assayed in a system using a sample diluent not containing *E. coli* LPS (Diluent 1) and systems using the same diluent supplemented with *E. coli* LPS at the various concentrations shown in Table 5. The line color development in the test region and control region was evaluated from the line intensity measured with a densitometer (manufactured by ATTO). The results are shown in Table 5.

TABLE 5

| | | | Level of addition of *E. coli* LPS (μg/ml) | | | | |
|---|---|---|---|---|---|---|---|
| | | Diluent 1 | 100 | 33.3 | 11.1 | 3.7 | 1.2 |
| Positive urine | Control site | 50 | 51 | 43 | 36 | 41 | 45 |
| | Test site | 68 | 66 | 62 | 61 | 61 | 67 |
| Negative urine | Control site | 26 | 26 | 22 | 18 | 23 | 23 |
| | Test site | 12 | 0 | 0 | 0 | 13 | 12 |

It was found that when *E. coli* LPS was added to the sample at 11.1 μg/ml and higher levels, the nonspecific reaction observed with Diluent 1 disappeared so that a false positive test (detection error) could be precluded.

INDUSTRIAL APPLICABILITY

The present invention provides an antibody assay technology by which target antibodies specific to sources of infection can be detected with high sensitivity and high specificity even when urine samples which are comparatively lean in the antibodies are used as test samples. According to the antibody assay method of the invention, the "false positive" reactions due to contaminants in samples can be significantly inhibited so that highly accurate and dependable assay results can be obtained. Moreover, the present invention provides improvements in immunocapillary or immunochromatographic assays, whereby the existence of target antibodies and their amounts in samples can be detected accurately with a clear distinction between "false negative" and "true negative".

The invention claimed is:

1. A method for suppressing a non-specific reaction in an immunoassay used to detect a target antibody in a urine sample, comprising:
  (A) applying a solution to a solid support having an assay antigen immobilized thereon, but not having *E. coli* derived substances immobilized thereon, wherein said solution comprises:
    (i) a urine sample comprising
      (a) a non-specific antibody component, and
      (b) a target antibody; and
    (ii) an *E. coli* component;
  wherein said assay antigen is selected from the group consisting of a pathogen, an inactivated pathogen and an antigen extracted from a pathogen; wherein said pathogen is a human or animal pathogen; and wherein said pathogen is not *E. coli*; and
  (B) detecting binding of said target antibody to said assay antigen with a labeled secondary antibody that binds to said target antibody,
  whereby said *E. coli* component suppresses a non-specific reaction between said non-specific antibody component and said labeled secondary antibody.

2. The method for suppressing a non-specific reaction according to claim 1, wherein the *E. coli* component is at least one member selected from the group consisting of a soluble fraction and a lipopolysaccharide fraction of *E. coli*.

3. The method for suppressing a non-specific reaction according to claim 1, wherein the target antibody is an antibody against a source of infection selected from the group consisting of a virus, a bacteria, and a protozoa.

4. The method for suppressing a non-specific reaction according to claim 1, wherein the target antibody is an antibody against *Helicobacter pylori*.

5. The method for suppressing a non-specific reaction according to claim 1, wherein the source of said assay antigen is selected from the group consisting of human immunodeficiency virus, hepatitis virus, rubella virus, influenza virus, measles virus, herpes virus, cytomegalovirus, Clamydia, gonococci, *Helicobacter pylori* and *Toxoplasma gondii*.

6. The method for suppressing a non-specific reaction according to claim 1, wherein said assay antigen is selected from the group consisting of a bacteria, a virus, a protozoa, a component of a bacteria comprising an antigenic determinant group of the bacteria, a component of a virus comprising an antigenic determinant group of the virus, and a component of a protozoa comprising an antigenic determinant group of the protozoa.

7. The method for suppressing a non-specific reaction according to claim 1, wherein said assay antigen is *Helicobacter pylori* or a component of *Helicobacter pylori* which comprises an antigenic determinant group of *Helicobacter pylori*.

8. The method for suppressing a non-specific reaction according to claim 1, wherein the *E. coli* component is selected from the group consisting of a protein component of *E. coli*, a carbohydrate component of *E. coli*, a lipid component of *E. coli*, and a mixture thereof.

9. The method for suppressing a non-specific reaction according to claim 1, wherein the immunoassay is carried out by the sandwich technique.

10. A reagent kit for carrying out the method for suppressing a non-specific reaction according to claim 1, comprising an antigen for detecting the target antibody and an *E. coli* component.

* * * * *

UNITED STATES PATENT AND TRADEMARK OFFICE
CERTIFICATE OF CORRECTION

PATENT NO.        : 7,368,277 B2
APPLICATION NO.   : 10/386562
DATED             : May 6, 2008
INVENTOR(S)       : Tetsuya Tachikawa et al.

It is certified that error appears in the above-identified patent and that said Letters Patent is hereby corrected as shown below:

On the Title Page Item (73) Assignee should read: Otsuka Pharmaceutical ~~Factory, Inc.,~~ Co., Ltd., Tokyo (JP)

Signed and Sealed this

Eighth Day of September, 2009

David J. Kappos
*Director of the United States Patent and Trademark Office*